United States Patent
Avneri et al.

(10) Patent No.: US 9,693,795 B2
(45) Date of Patent: Jul. 4, 2017

(54) DEVICES AND METHODS FOR MINIMALLY INVASIVE TISSUE REMOVAL

(71) Applicant: ANGIOWORKS MEDICAL, B.V., Amsterdam (NL)

(72) Inventors: Itzhak Avneri, Tel Aviv (IL); Rami Lore, Kiyat Tivon (IL); Gonen Yuval, Kiyat Tivon (IL); Shahar Avneri, Herzliya (IL)

(73) Assignee: ANGIOWORKS MEDICAL B.V., Amsterdam (NL)

( * ) Notice: Subject to any disclaimer, the term of this patent is extended or adjusted under 35 U.S.C. 154(b) by 0 days.

(21) Appl. No.: 15/167,629

(22) Filed: May 27, 2016

(65) Prior Publication Data

US 2016/0346002 A1     Dec. 1, 2016

Related U.S. Application Data

(60) Provisional application No. 62/167,089, filed on May 27, 2015.

(51) Int. Cl.
*A61B 17/22* (2006.01)
*A61B 17/3207* (2006.01)
(Continued)

(52) U.S. Cl.
CPC .... *A61B 17/320725* (2013.01); *A61B 17/221* (2013.01); *A61B 17/32056* (2013.01);
(Continued)

(58) Field of Classification Search
CPC .......... A61B 17/221; A61B 17/320725; A61B 17/32056; A61B 2017/2212;
(Continued)

(56) References Cited

U.S. PATENT DOCUMENTS

| 3,730,185 A | 5/1973 | Cook et al. |
| 4,739,760 A | 4/1988 | Chin et al. |

(Continued)

FOREIGN PATENT DOCUMENTS

| WO | WO-01/35839 A2 | 5/2001 |
| WO | WO-2004/019816 A2 | 3/2004 |

(Continued)

OTHER PUBLICATIONS

EP Appln No. 12838492: Supplementary European Search Report mailed Feb. 18, 2015.
(Continued)

*Primary Examiner* — Ashley Fishback
(74) *Attorney, Agent, or Firm* — Michele V. Frank; Venable LLP

(57) ABSTRACT

A medical device for minimally invasive removal of tissue from a body lumen, can include: a sheath having a proximal and a distal end; and a tool configured to pass through the sheath and configured to transition from a crimped state to a deployed state and to a closed state, wherein the tool forms an aperture at a distal end, the distal end of the tool having at least one tube loop and at least one wire loop, wherein the tool is configured to dissect tissue in the deployed state.

30 Claims, 20 Drawing Sheets

(51) Int. Cl.
*A61B 17/3205* (2006.01)
*A61B 17/221* (2006.01)
*A61B 17/00* (2006.01)

(52) U.S. Cl.
CPC ............... *A61B 2017/00778* (2013.01); *A61B 2017/2215* (2013.01); *A61B 2017/320741* (2013.01)

(58) Field of Classification Search
CPC .. A61B 2017/2215; A61B 2017/00778; A61B 2017/320741
See application file for complete search history.

(56) References Cited

U.S. PATENT DOCUMENTS

| | | | |
|---|---|---|---|
| 4,832,688 | A | 5/1989 | Sagae et al. |
| D307,323 | S | 4/1990 | Scanlan |
| 5,102,415 | A | 4/1992 | Guenther et al. |
| 5,653,726 | A | 8/1997 | Kieturakis |
| 5,728,123 | A | 3/1998 | Lemelson et al. |
| 5,782,840 | A * | 7/1998 | Nakao ................... A61B 18/14 606/110 |
| 5,782,848 | A | 7/1998 | Lennox |
| 5,906,622 | A | 5/1999 | Lippitt et al. |
| 5,947,985 | A | 9/1999 | Imran |
| 5,954,713 | A | 9/1999 | Newman et al. |
| 6,146,397 | A | 11/2000 | Harkrider, Jr. |
| 6,241,745 | B1 | 6/2001 | Rosenthal |
| 6,328,749 | B1 | 12/2001 | Kalmann et al. |
| 6,506,178 | B1 | 1/2003 | Schubart et al. |
| 6,565,583 | B1 | 5/2003 | Deaton et al. |
| 6,635,070 | B2 | 10/2003 | Leeflang et al. |
| 6,652,548 | B2 | 11/2003 | Evans et al. |
| 6,679,893 | B1 | 1/2004 | Tran |
| 6,695,858 | B1 | 2/2004 | Dubrul et al. |
| 6,719,775 | B2 | 4/2004 | Slaker et al. |
| 6,945,977 | B2 | 9/2005 | Demarais et al. |
| 7,108,704 | B2 | 9/2006 | Trerotola |
| 7,210,210 | B2 | 5/2007 | Lippitt et al. |
| 7,517,352 | B2 | 4/2009 | Evans et al. |
| 7,833,240 | B2 | 11/2010 | Okushi et al. |
| 7,955,350 | B2 | 6/2011 | Konstantino et al. |
| 8,012,117 | B2 | 9/2011 | Bonnette et al. |
| 8,057,496 | B2 | 11/2011 | Fischer, Jr. |
| 8,142,457 | B2 | 3/2012 | Lafontaine |
| 8,298,244 | B2 | 10/2012 | Garcia et al. |
| 9,017,328 | B2 | 4/2015 | Bahney |
| 9,216,034 | B2 | 12/2015 | Avneri et al. |
| 2002/0029052 | A1 | 3/2002 | Evans et al. |
| 2002/0082592 | A1 | 6/2002 | Lary |
| 2003/0120195 | A1 | 6/2003 | Milo et al. |
| 2004/0193204 | A1 | 9/2004 | Lafontaine |
| 2004/0199200 | A1 * | 10/2004 | Teague ................. A61B 17/221 606/200 |
| 2006/0195137 | A1 | 8/2006 | Sepetka et al. |
| 2007/0208370 | A1 | 9/2007 | Hauser et al. |
| 2009/0099581 | A1 | 4/2009 | Kim et al. |
| 2010/0318178 | A1 | 12/2010 | Rapaport et al. |
| 2011/0144671 | A1 | 6/2011 | Piippo Svendsen et al. |
| 2013/0317515 | A1 | 11/2013 | Kuroda et al. |
| 2014/0128894 | A1 | 5/2014 | Sepetka et al. |
| 2014/0276809 | A1 * | 9/2014 | Smith ............... A61B 17/32056 606/46 |
| 2014/0296889 | A1 | 10/2014 | Avneri et al. |
| 2014/0364868 | A1 | 12/2014 | Dhindsa |
| 2015/0066047 | A1 | 3/2015 | Chu et al. |
| 2015/0119896 | A1 | 4/2015 | Krolik et al. |
| 2015/0342624 | A1 | 12/2015 | Lippitt et al. |

FOREIGN PATENT DOCUMENTS

| | | |
|---|---|---|
| WO | WO-2009/120205 A1 | 10/2009 |
| WO | WO-2013/050880 A2 | 4/2013 |

OTHER PUBLICATIONS

PCT/IB2012/002847: International Search Report and Written Opinion, mailed Apr. 29, 2013.
Holzapfel et al., "Anisotropic Mechanical Properties of Tissue Components in Human Atherosclerotic Plaques," Journal of Biomedical Engineering, 2004; 126:657-665.
Scholtes et al., "Subintimal Angioplasty Track of the Superficial Femoral Artery A Histological Analysis," Circ. Cardiovasc. Interv. 2012;5:e6-e8.
Sobieszczyk, MD Piotr, "Catheter-Assisted Pulmonary Embolectomy", Circulation. 2012;126:1917-1922.
International Search Report and Written Opinion mailed Sep. 20, 2016 in corresponding International Application No. PCT/IB2016/000891.

* cited by examiner

DEVICES AND METHODS FOR MINIMALLY INVASIVE TISSUE REMOVAL

CROSS-REFERENCE TO RELATED APPLICATIONS

This application claims priority to U.S. Provisional Application No. 62/167,089 filed May 27, 2015, which is incorporated herein in its entirety by reference.

TECHNICAL FIELD

This application relates to devices and methods for minimally invasive tissue removal, and specifically for removing tissue using remote endarterectomy.

BACKGROUND

The normal human artery is composed of three main layers. The innermost layer lining the artery, in contact with the blood, is the intima. This is a single cell layer of endothelial cells, which among other functions regulates vascular tone, platelet activation and thrombus formation, monocyte adhesion and inflammation and vascular remodeling. The media—the middle layer, consists of several layers of smooth muscle cells and elastic fibers. The outermost layer is the adventitia, which is mainly composed of connective tissue containing small blood vessels and nerves.

Atherosclerosis is one of the major causes of cardiovascular cerebrovascular and peripheral vascular morbidity and mortality. It is a disease of large and medium-sized muscular arteries, which is characterized by the formation of discrete lesions called atherosclerotic plaques, or atheromas, thought to be caused by injury to the endothelium. An atheroma is a buildup of lipids, cholesterol, calcium, and cellular debris within the intima of the vessel wall. Atherosclerotic buildup also results in vascular remodeling, acute and chronic luminal obstruction, abnormalities of blood flow and diminished oxygen supply to target organs.

Manifestations of atherosclerotic disease depend on the affected organs and the type of lesions. Chronically narrowed arteries give rise to symptoms of insufficient blood flow such as angina pectoris (chest pain during exertion), intermittent claudication (leg pain during exertion), and chronic leg ulcers. Acute events can occur as a result as of plaque rupture and thrombosis, which might totally clog the artery as in most cases of acute myocardial infarction (heart attack), or as a result of distal embolization of plaque fragments, as in many cases of stroke.

Treatment of atherosclerosis depends on many factors including the location of symptomatic lesions, the severity of symptoms, and their dynamics.

Acute obstruction events usually require acute intervention. For acute coronary events, treatment is urgent percutaneous angioplasty (balloon dilation of the obstructed artery) and stenting. Depending on the time from the beginning of symptoms, acute ischemic stroke is sometimes treated urgently by percutaneous mechanical removal of the obstruction or injection of compounds that lyse it (tPA, streptokinase), but in many such cases treatment will only focus on the prevention of future events. Acute limb ischemia is also treated by urgent revascularization, either percutaneous or surgical.

The treatment of chronic obstruction can include an interventional procedure, which may be surgical or percutaneous and is aimed at revascularization of the target organs and removal of a potential source of emboli, if present.

Surgical treatments include bypass surgery, more commonly used for coronary and lower limb arteries, and endarterectomy, which is used for limb and carotid arteries, and involves opening the artery and removing the plaque along with the intima. Obviously, the disadvantage of surgery is its highly invasive nature, the need for anesthesia, and the pain and stress involved which make it unsuitable for certain patients.

Percutaneous procedures enable treating the lesions using long catheters inserted to the arteries at a distant point such as the groin arteries. The most common of these is placement of a stent, a metal structure which is inserted to the artery in a closed state and expanded within the lesion so as to keep the lumen patent. This can be done with or without balloon angioplasty (inflation of a balloon in the lesion to enlarge the lumen prior to or following stent placement). The main disadvantage of angioplasty and stenting is that the plaque remains in the artery. This has several deleterious consequences. First—in carotid stenting, many of the post stenting strokes are caused not during the procedure, but after it, and are probably related to plaque material squeezing through the cells of the stent and embolizing to the brain (a phenomenon known as the "mashed potato effect"). Second—in many cases the plaque encroaches on the stent and does not enable attainment of a normal vascular lumen. This in turn affects flow dynamics and shear stress, which may enhance atherogenesis and cause restenosis. Third—the plaque material itself contains many inflammatory and prothrombotic substances. This may be the reason for the high rate of restenosis experienced after stenting.

What is needed are methods, devices and systems for improving procedures for removing tissue.

SUMMARY

A medical device for minimally invasive removal of tissue from a body lumen, can include: a sheath having a proximal and a distal end; and a tool configured to pass through the sheath and configured to transition from a crimped state to a deployed state and to a closed state, wherein the tool forms an aperture at a distal end, the distal end of the tool having at least one tube loop and at least one wire loop. The tool can be configured to dissect tissue in the deployed state.

The tissue can be a lesion and the tool can be configured to extend along the lesion and can be configured to dissect around the lesion along a longitudinal axis of the body lumen.

The tool can be configured to close the aperture distal to the dissected tissue to contain the tissue and the tool can be configured to remove the tissue in the closed state.

The tool can include a plurality of tube loops and a plurality of wire loops. The wire loops can be moveable to a plurality of locations with respect to a radial axis of the sheath, the wire loops can be configured to contact each other, and the wire loops can be configured to close such that a scissor action between adjacent wires is operable to cut intima of the tissue.

In a radial axis of the sheath, each wire loop can extend under another wire loop and over another wire loop. Each tube loop can have a first and a second wire loop, and from a distal end view in the radial axis of the sheath, the second wire loop can extend under the first wire loop in a clockwise direction of the radial axis of the sheath.

Each of a first set of two opposing wire loops can extend over one of a second set of opposing wire loops, and each of the second set of opposing wire loops can extend under one of the first set of opposing wire loops in a radial axis of the sheath. One wire loop can extend over adjacent wire loops and an opposing wire loop can extend under adjacent wire loops. Each wire loop can have a pre-formed curvature around a radial axis of the sheath. The curvature can be radially displaced from a longitudinal axis of the sheath.

At least one of the wire loops can extend over at least another wire loop and at least one of the wire loops can extend under at least another of the wire loops in the radial axis of the sheath.

A first wire loop can extend over all other wire loops and other wire loops can be interlaced with adjacent wire loops in the radial axis of the sheath. The first wire loop when retracted can be configured to pass a center line of the body lumen.

Each tube loop can have a first wire loop that extends in a counter-clockwise direction of the radial axis of the sheath and a second wire loop that extends in a clockwise direction of the radial axis of the sheath.

The first and second wire loops can cross each other in the radial axis. The first and second wire loops may not cross each other in the radial axis.

The at least one wire loop can be graded in the deployed state. The graded wire loops can protrude from the distal end of the sheath at varying distances.

The wire loops can have a graded distance between a most distal wire loop distal end and a most proximal wire loop distal end. The graded distance can provide improved entry of the tool to subintimal space.

The at least one tube loop can have a window that allows for passage of the at least one wire loop. The window of the at least one tube loop can be a distal window and can outline two holes.

The at least one tube loop can have a longitudinal axis, and the distal window can have a length along the longitudinal axis in a range between about 0.5 to about 5 times a diameter of the at least one tube loop.

The at least one tube loop can include four spatially equidistant loops.

The at least one tube loop comprises anywhere from two through eight loops. The device can further include: a handle at a proximal portion of the sheath; and a multilumen tube disposed inside at least a portion of the sheath, the multilumen tube being configured to interface with the at least one tube loop. The tool can be configured to pass through the distal end of the sheath using movement of the handle. The handle can include an elongate casing having a wire handle connected to the at least one tube loop and a slot for the wire handle to slide, and the multilumen tube can be disposed inside at least a portion of the casing.

The device can further include a sac that is configured to enclose the at least one tube loop and at least one wire loop in the closed state. At least a portion of the sac can be disposed inside the sheath. At least a portion of the sac can be disposed outside the sheath.

The device can further include a ring that is slideably disposed between the multilumen tube and the sheath, where the sac is connected to the ring. The sac can be connected to at least one portion of the distal end of the at least one tube loop. The sac can be connected to at least one portion of the distal end of the at least one wire loop.

The device can further include a cutting element that is located at the distal end of the at least one tube loop. The cutting element can be configured to expand radially with expansion of the aperture. The cutting element can surround the aperture of the tool.

The cutting element can include a blunt and a sharp state. The cutting element can be configured to transition between blunt and sharp states upon the aperture substantially closing.

The tool in the deployed state can have a radial force and the tool is configured to allow adjustment of at least one of the radial force and the aperture. The at least one tube loop can have an adjustable outward angle and the adjustment of the radial force can take place by pushing the at least one wire loop along a longitudinal axis of the sheath. The at least one wire loop can have varying degrees of rigidity and the adjustment of the radial force can be by shifting a location of segments of the at least one wire loop.

The at least one tube loop and the at least one wire loop can include three levels of loops. The tool can include a first level of at least one tube loop and a second level of at least one tube loop that proceeds from a distal end of the first level of the at least one tube loop in the deployed state. The at least one wire loop can extend from the distal end of the second level of at least one tube loop in the deployed state.

The tool can include a directional feature that ensures order and orientation of the at least one tube loop. The device can further include a multilumen segment that is configured to house at least a portion of the at least one tube loop. The directional feature can include the tube loop having a portion with an oval cross-sectional shape and a central lumen of the multilumen segment having an oval cross-sectional shape.

The device can further include a multilumen segment that is configured to house at least a portion of the tube loop. The device can further include connections between each of adjacent tube loops. The connections can be distal to the multilumen segment.

The at least one tube loop can form a cross-section of the device that has a generally circular shape. The at least one tube loop can be expandable. The at least one tube loop can be radially expandable.

The tool can be at least one of self-expandably, slideably and rotatably disposed in the sheath. The at least one tube loop can be configured to remove a plaque from an arterial wall. The at least one tube loop can be adjustable.

The at least one tube loop can include a sharp element at the distal end. The distal end of the at least one tube loop can include a blunt portion that is oriented away from an arterial wall of the body lumen and a sharp portion having the sharp element that protrudes into the tissue to be removed.

The at least one tube loop can be an arch having two legs along a longitudinal axis of the sheath in the deployed state. The arch can have a curved symmetrical structure spanning an opening.

The at least one wire loop can be a monofilament wire of shape memory material. The at least one wire loop can be made of nitinol.

The at least one tube loop can be hollow to surround the at least one wire loop in the crimped state, and the at least one wire loop can be exit-able/extendable from the at least one tube loop.

A diameter of the at least one wire loop can be less than an inner diameter of the at least one tube loop. The minimally invasive removal of tissue can be percutaneous access removal of tissue.

The device can be configured for the minimally invasive removal of tissue in an endarterectomy. The device can be configured for the minimally invasive removal of blood clot in an embolectomy. The device can be configured for the minimally invasive removal of renal calculi in an urolithotomy. The device can be configured for the minimally invasive removal of tissue in a pulmonary embolism.

A method for minimally invasively removing tissue from a body lumen, can include: passing a tool through a sheath that is configured to transition from a crimped state to a deployed state and to a closed state, a distal end of the tool having at least one tube loop and at least one wire loop; forming an aperture at a distal end of the tool in the deployed state; and dissecting tissue in the deployed state.

The forming the aperture step can include extending the wire loops. The extending the at least one wire loop can include advancing the at least one wire loops through at least one window of the at least one tube loop. The passing the tool through the sheath includes transitioning to an expanded state.

In the method, the tissue can be a lesion and the method can further include extending the tool along the lesion. The dissecting can include dissecting the lesion along a longitudinal axis of the body lumen.

The method can further include: closing the aperture distal to the dissected tissue to contain the tissue; and removing the tissue in the closed state.

In the method, the tool can include a handle at a proximal portion of the sheath; and a multilumen tube disposed inside at least a portion of the sheath, the multilumen tube being configured to interface with the at least one tube loop, and the method can further include passing the tool through the distal end of the sheath using movement of the handle. The handle can include an elongate casing having a wire handle connected to the at least one tube loop and a slot for the wire handle to slide, and the multilumen tube can be disposed inside at least a portion of the casing.

The method can further include enclosing the loops with a sac in the closed state. The method can further include passing the at least one wire loop through windows of the at least one tube loop in the deployed state.

The method can further include utilizing a cutting element to remove the tissue. The method can further include inserting a wire loop into the subintimal space of the tissue; and threading a leading wire loop distal end over a wire which has been inserted into the subintimal space of the tissue.

The method can further include: housing at least a portion of the at least one tube loop with a multilumen segment; and providing connections between each of adjacent tube loops distal to the multilumen segment.

The at least one tube loop can have a graded distance of the distal ends for the tool's improved entry to the subintimal space of the tissue.

The minimally invasive removal of tissue can include an endarterectomy. The minimally invasive removal of tissue can include an embolectomy. The minimally invasive removal of tissue can treat a pulmonary embolism. The minimally invasive removal of tissue can include a percutaneous procedure. The minimally invasive removal of tissue can include a urolithotomy.

Additional features, advantages, and embodiments of the invention are set forth or apparent from consideration of the following detailed description, drawings and claims. Moreover, it is to be understood that both the foregoing summary of the invention and the following detailed description are examples and intended to provide further explanation without limiting the scope of the invention as claimed.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

In accordance with current needs, embodiments of the present invention provide a low profile device for performing percutaneous subintimal remote endarterectomy, by opening an "aperture" proximal to an atherosclerotic lesion, extending it distally to a long distance, while dissecting tissue around the interior of the vessel and containing it within a sheath, then closing the "aperture" beyond the lesion, or at an arbitrary point along the lesion, and removing the excised tissue from the patient's body.

Figure 1A:
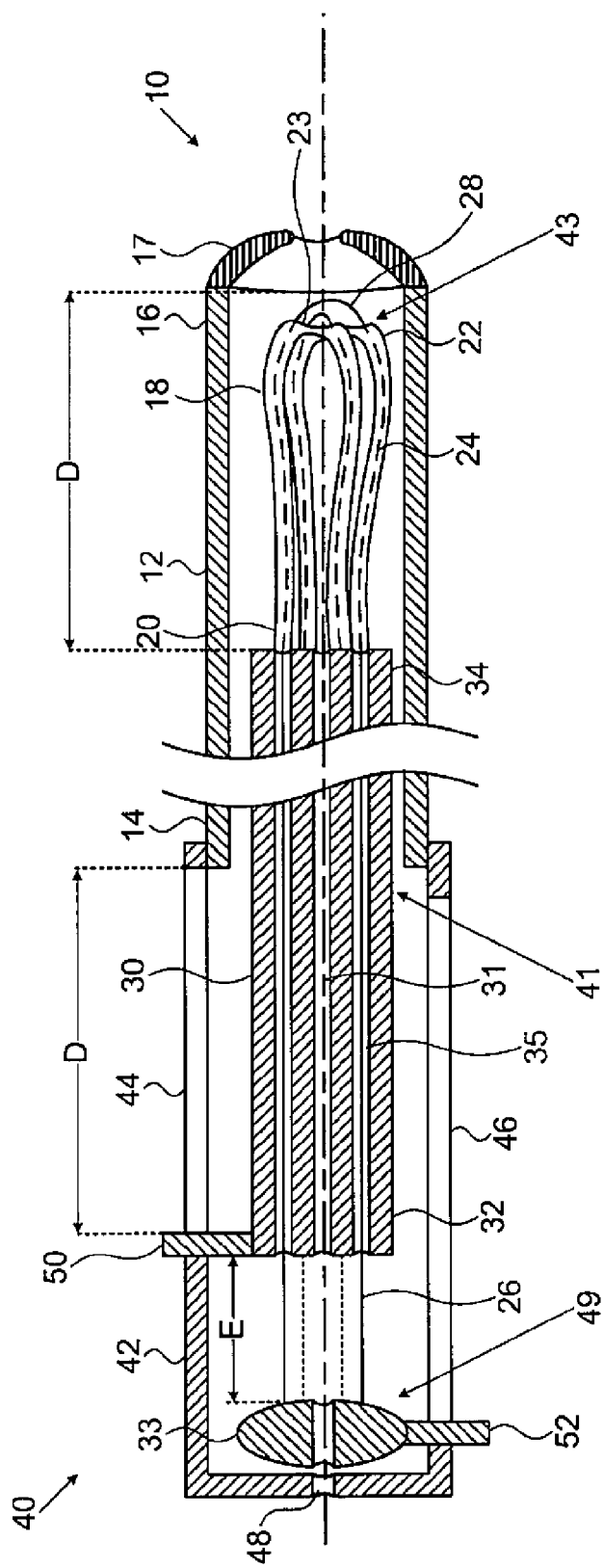
FIG. 1A shows a longitudinal cross-section view of a medical device for percutaneous removal of tissue in a crimped state, according to an embodiment of the invention.
Figure 1B:
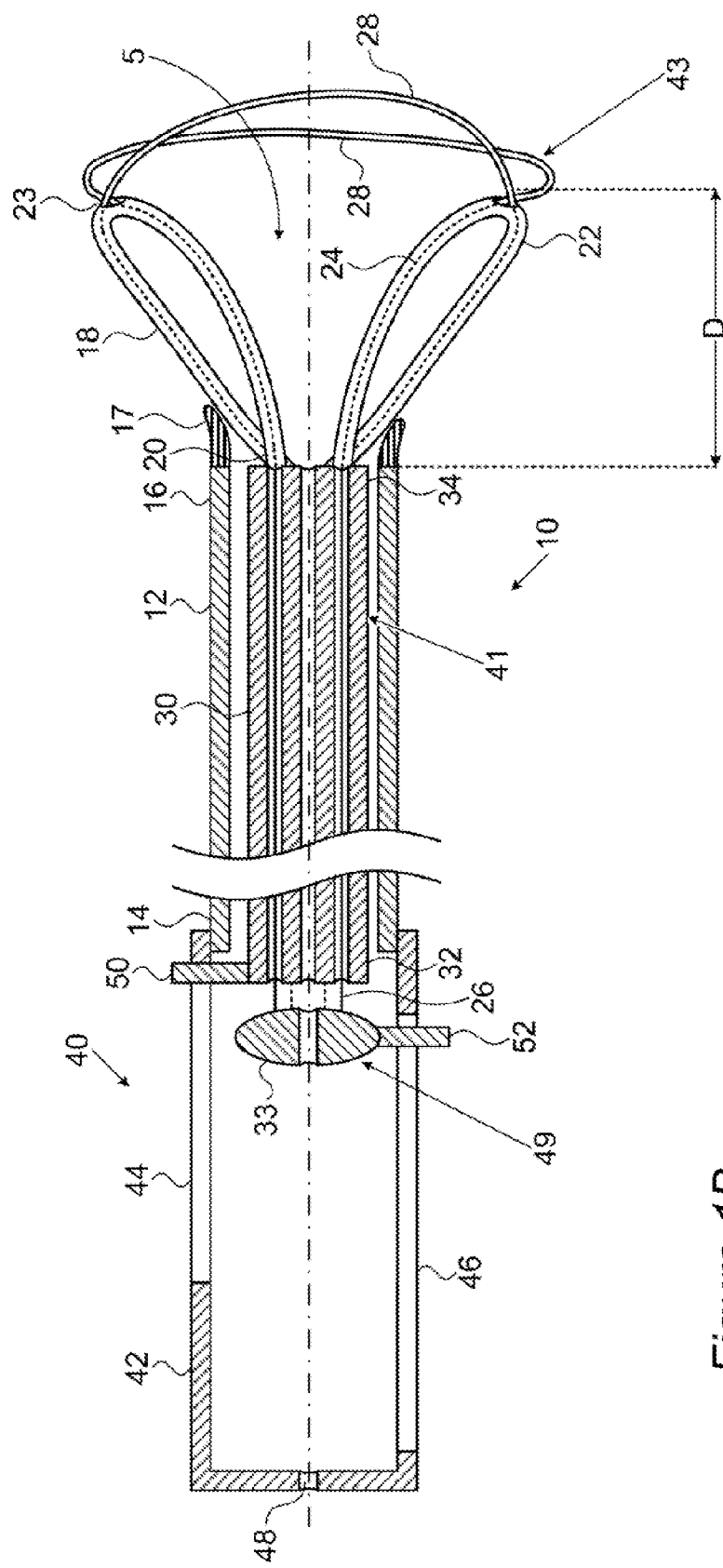
FIG. 1B shows a longitudinal cross-section view of a medical device for percutaneous removal of tissue in a deployed state, according to an embodiment of the invention.

An embodiment of an improved percutaneous remote endarterectomy device 10 is depicted in FIGS. 1A & 1B, which are simplified schematic drawings of longitudinal sections of device 10 in its crimped and deployed states respectively. FIGS. 1A and 1B show a device for minimally invasive removal of tissue from a body lumen that can include a sheath 12 having a proximal end 14 and a distal end 16. The device can include a tool 41 configured to pass through the sheath 12, and transition from a crimped state to a deployed state and to a closed state. The tool 41 can form an aperture at a distal end. The tool 41 can be configured to dissect tissue in the deployed state. In an embodiment, the tissue can be a lesion and the tool can be configured to extend along the lesion and can be configured to dissect the lesion along a longitudinal axis of the body lumen. Further, the tool can be configured to dissect around the lesion along the longitudinal axis of the body lumen. The tool can be configured to close the aperture distal to the dissected tissue to contain the tissue. The tool can be configured to remove the tissue in the closed state. The tool can be at least one of self-expandably, slideably and rotatably disposed in the sheath.

The distal end 43 of the tool 41 can have a tube loop 18 and a wire loop 28. The distal end 43 of the tool 41 can include a plurality of tube loops 18 and a plurality of wire loops 24. Reference that is made to a tube loop or a wire loop is also meant to include a plurality of tube loops and/or a plurality of wire loops, respectively. The one or more wire loops 24 can extend from a distal end 22 of the one or more tube loops 18. In an embodiment, the plurality of tube loops can include anywhere from two through eight loops. The at least one tube loops can be expandable in the longitudinal and radial axis of the sheath.

The one or more tube loops can have a substantially linear shape at a proximal end 20 along the longitudinal axis of the sheath 12. The at least one tube loops can be expandable in relation to the sheath in both a longitudinal and radial direction. The at least one tube loop can be adjustable in relation to the at least one wire loop. That is, at a stationary position, the at least one wire loop can expand longitudinally and/or radially with regard to the at least one tube loop.

More particularly, FIG. 1A is a schematic longitudinal section of device 10 in its crimped state, mainly comprising the following parts, from proximal to distal: handle 40, which operates a multilumen tube 30, one or more tube loops 18 and one or more wire loops 24, which are slideably disposed within a sheath 12 having proximal end 14 and distal end 16, and optionally an atraumatic tip 17.

Tube loops 18 have proximal ends 20, and distal ends 22 having window 23. Wire loops 24 are slideably disposed within tube loops 18, and have proximal ends 26, and distal ends 28, protruding outwardly and distally through window 23 of tube loop distal ends 22.

The number of tube loops 18 and wire loops 24 can be equal, and may be one or more, but is typically 3-5, preferably 4. For the sake of clarity, only two of tube loops 18 and wire loops 24 are shown in FIGS. 1A and 1B.

Multilumen tube 30 having proximal end 32 and distal end 34 may be slideably disposed within sheath 12 proximal to tube loops 18. Multilumen tube 30 may have a central lumen 31, and peripheral lumens 35, typically numbering double the number of tube loops 18. Proximal end 20 of tube loops 18 may be connected to distal end 34 of multilumen catheter 30, such that the lumens of tube loops 18 and multilumen catheter 30 are continuous, and wire loops 24 pass through multilumen catheter 30, exiting at its proximal end 32, and connecting to connector 33.

In an embodiment, multilumen catheter 30 can be omitted and tube loops 18 made longer so as to span the length of sheath 12, although the prior design saves in tube length and is therefore more economical.

Device 10 may be controlled by a handle 40 comprised of an elongate casing 42 which may have a short slot 44, a long slot 46, and an opening 48. Casing 42 may be attached to proximal end 14 of sheath 12. A tube handle 50 may be provided in the form of a protrusion from proximal end 32 of multilumen catheter 30, and a wire handle 52 may be provided in the form of a protrusion from connector 33. Tube handle 50 may protrude through casing 42 via short slot 44, and wire handle 52 may protrude through casing 42 via long slot 46.

Device 10 typically has a through lumen along its center, enabling passage of a guidewire for navigation, guidance, stabilization, manipulation, or other uses. The guidewire may be passed through distal tip 16 of sheath 12, and central lumen 31 of multilumen tube 30, and may exit device 10 proximally through opening 48. A dedicated tube (not shown) may optionally be further added to device 10 to define the through lumen and facilitate guidewire passage through the above route or any other route.

Thus, the device 10 can include a handle 40 at a proximal portion 49 of the device 10 and a multilumen tube 30 disposed inside at least a portion of the sheath. The multilumen tube 30 can be configured to interface with the at least one tube loop. The tool 41 can be configured to pass through the distal end 16 of the sheath 12 using movement of the handle 40. The multilumen tube 30 can be a multilumen sheath or a multilumen catheter. The handle can include an elongate casing 42 having a wire handle 52 connected to the at least one tube loop and a slot for the wire handle to slide. The multilumen tube 30 can be disposed inside at least a portion of the casing 42.

The above design of the handle 40 is a simplified basic design described just as an example. Various different designs for handles of endovascular devices as known in the art may be used to increase control and precision of deployment, for example using cog wheels and toothed rods to advance multilumen tube 30, and various types of sliding or rotating latches or buttons to advance connector 33.

In the crimped state of device 10, the distance D between tube handle 50 and distal end of short slot 44 may be approximately equal to the length of tube loops 18. This distance defines the maximal length of endarterectomy which may be achieved in a single deployment of device 10.

In the crimped state of device 10, the distance between wire handle 52 and proximal end 32 of multilumen tube 30 is E. This distance determines the maximal radial opening of distal end 43 of tool 41 in the deployed state, by affecting the distance between distal ends 22 of tube loops 18.

FIG. 1B is a schematic longitudinal section of device 10 in its deployed state, and shows the same parts depicted in FIG. 1A, including, from proximal to distal: handle 40, multilumen tube 30, sheath 12, optional atraumatic tip 17, tube loops 18 and wire loops 24.

More particularly, in FIG. 1B, tube handle 50 was pushed to the distal end of short slot 44, moving multilumen tube 30 distally, and passing tube loops 18 beyond distal tip 16. Wire handle 52 was also pushed to distal end of long slot 46, deploying wire loops 24 out of tube loops 18, thus opening an "aperture" 5. Aperture 5 is defined by the opening created between deployed wire loop ends 28 and tube loop ends 22.

Figure 2A:
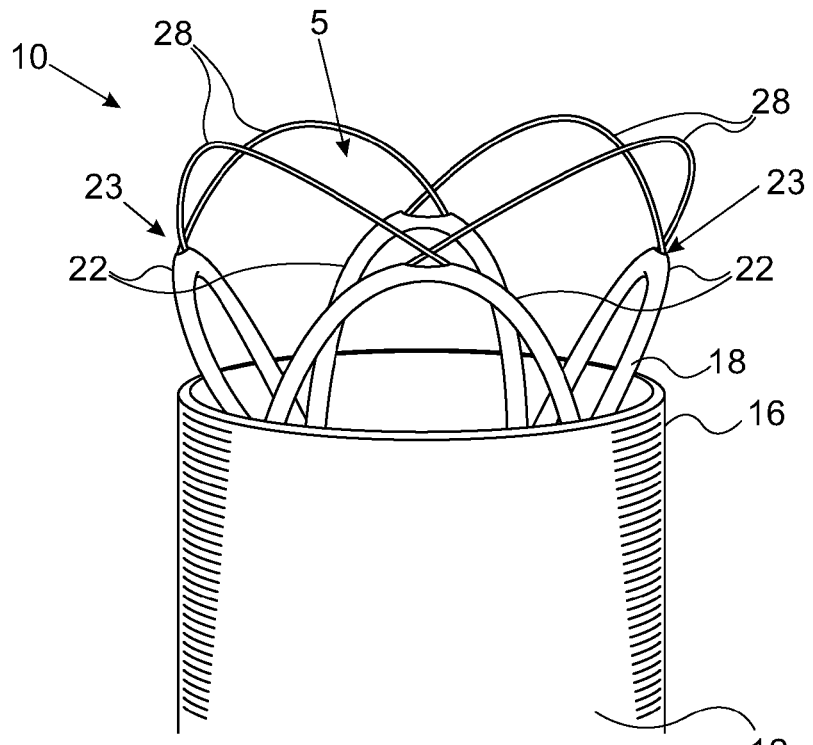
FIG. 2A shows a distal end of a medical device for percutaneous removal of tissue in a deployed state, according to an embodiment of the invention.

FIG. 2A is a 3D depiction of the distal end of device 10, having four tube loops 18 and wire loops 24, at the beginning of deployment.

More particularly, FIG. 2A shows distal end 16 of sheath 12, tube loops 18 with tube loops distal ends 22, windows 23, and wire loop distal ends 28 protruding therethrough.

Figure 2B:
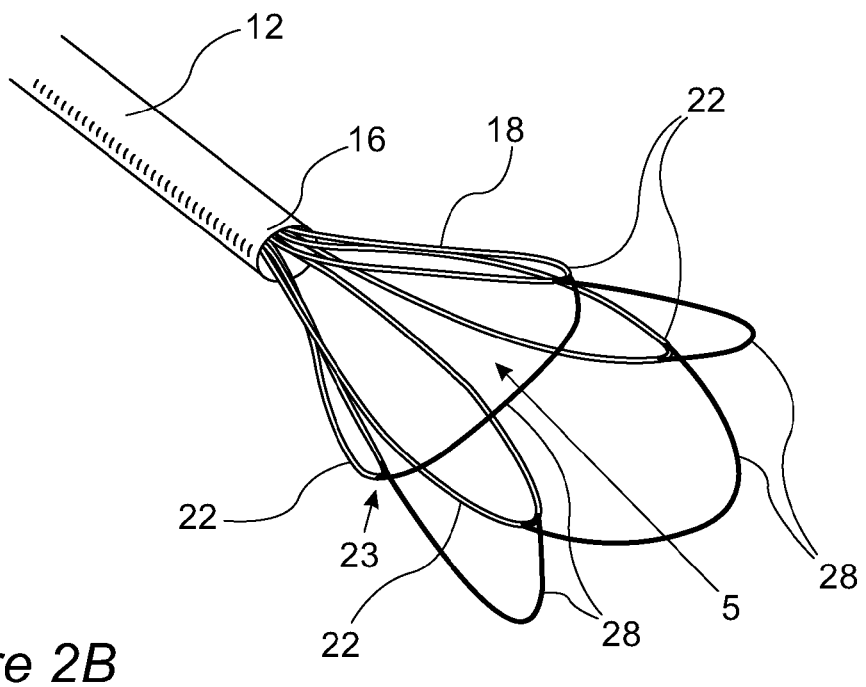
FIG. 2B shows a perspective view of a medical device in a deployed state, according to an embodiment of the invention.

In FIG. 2A, deployment is partial, as tube loops 18 have not yet fully extended radially beyond the perimeter of sheath 12. Ideally, at full deployment, tube loops 18 extend radially at least 3-4 times the diameter of sheath 12, as seen in FIG. 2B.

In use, crimped device 10 is typically inserted percutaneously into an artery, and advanced over a guidewire or via a guiding catheter, under fluoroscopic guidance, towards a previously identified atherosclerotic lesion requiring treatment. Thus, the minimally invasive removal of tissue can be through percutaneous access. That is, the device can be configured to be used in percutaneous procedures and techniques.

Once distal end 16 of sheath 12 is positioned proximal to the target lesion, typically at a distance of about 1-2 cm from the lesion, tool 41 is passed out of sheath 12 (e.g. by pushing tube handle 50 distally). This causes tube loops ends 22 to move distally out of sheath end 16. Pushing wire loops 24 distally (e.g. by pushing wire handle 52 distally) causes wire loop distal ends 28 to move distally out of windows 23, and increase the distance between tube loop distal ends 22. This causes the combined structure of tube loop distal ends 22 and wire loop distal ends to widen and extend radially, opening aperture 5 of device 10 into its deployed state.

The radial force of the deployed wire loops and tube loops pushes them against the artery and by the combined motion of distal pushing and rotation applied by the user, the wire loops dissect between a plaque and arterial wall into the subintimal space. Their position can be verified angiographically.

Dissection is continued until either the lesion is passed, or the maximal deployment distance (distance D) is reached. The physician can then pull wire handle 52 proximally, thus contracting aperture 5 at the distal end of the device. If the lesion was completely traversed and normal intima was reached, closure of aperture 5 may easily detach the dissected lesion from the distal intimal lining. If the closure is performed at mid lesion, greater pull force or one or more of the cutting elements and techniques described below may need to be utilized in order to cut through the lesion.

Once the aperture 5 has been closed, the lesion may become enclosed within tube loops 18 and optionally sac 80. It can then be pulled back towards the entry site. If too large to remove via the access sheath, the device with lesion in it may be extracted by removal of the sheath first, or using minimal surgical cut-down. Thus, the at least one tube loop can be configured to remove a plaque from an arterial wall.

Figure 2C:
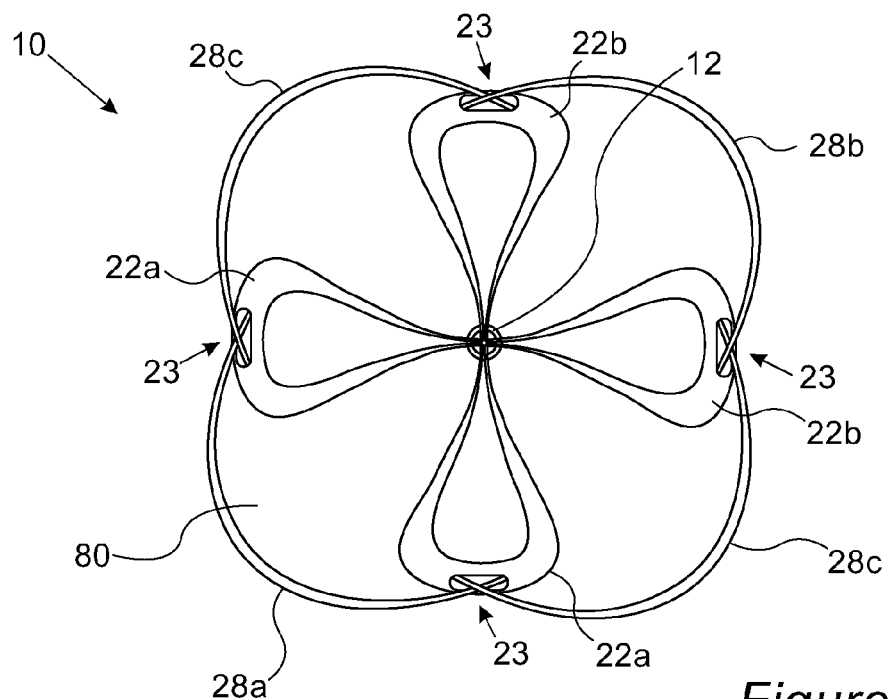
FIG. 2C is a perspective end view of a deployed device, according to an embodiment of the invention.

FIG. 2C is a perspective end view of deployed device 10.

More particularly, FIG. 2C is a perspective end view of a device 10 with four sets of loops, in its deployed state. FIG. 2C shows that the at least one tube loop can form a cross-section of the device that has a generally circular shape. Sheath 12 is seen at the center. Tube loops are seen exiting from sheath 12, ending at tube loop distal ends 22, with windows 23, from which are seen protruding wire loop distal ends 28.

The specific arrangement of wire loops and tube loops shown in the embodiment in FIG. 2C is the same as will be described herein in FIG. 4C. According to this arrangement, one wire loop distal end 28a may pass above adjacent wire loop distal ends 28c, and the opposite wire loop 28b may pass under adjacent wire loop distal ends 28*c*. As seen in FIG. 2C, aperture 5 may be formed by the combined structure of tube loop distal ends 22 and wire loop distal ends 28, and may have a substantially circular cross section.

Tube loop distal ends from which exit wire loop distal end 28*a*, are labeled tube loop distal ends 22*a*, while tube loop distal ends from which exit wire loop distal end 28*b*, are labeled tube loop distal ends 22*b*. Sac 80 may cover the loops.

Figure 2D:
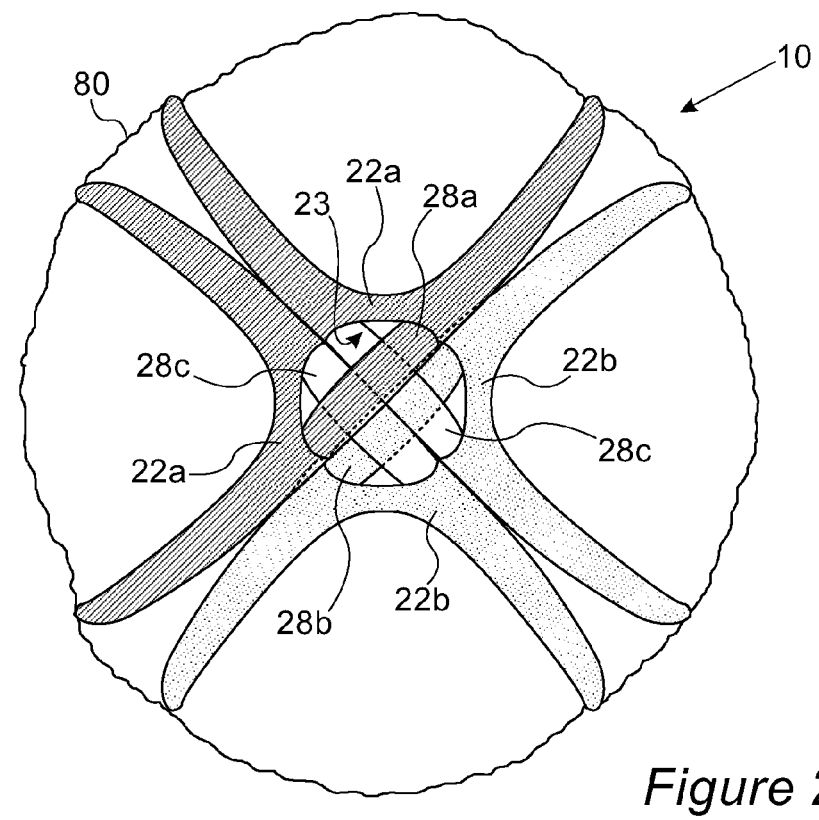
FIG. 2D is an end view of a device in a closed device, closed beyond dissected tissue, according to an embodiment of the invention.

FIG. 2D is a perspective end view device 10, closed beyond dissected tissue. More particularly, FIG. 2D is a perspective end view of a device 10 with four sets of loops, in its closed state beyond dissected tissue. From periphery to center, are seen: sac 80, covering tube loops 18 and containing dissected tissue, tube loop distal ends 28*a-b*, with windows 23, from which exit wire loop distal ends 28*a-c*.

The specific arrangement of wire loops and tube loops shown in the embodiment in FIG. 2D is the same as will be described herein in FIG. 4C, and as shown in FIG. 2C. According to this arrangement, one wire loop distal end 28*a* may pass above adjacent wire loop distal ends 28*c*, and the opposite wire loop 28*b*, may pass under adjacent wire loop distal ends 28*c*.

At the center of FIG. 2D are seen wire loops 28*a-c*, creating a complete closure of aperture 5. Due to the specific arrangement of wires and loops, wire loop distal end 28*a* may be slightly above (i.e., distal to) two wire loop distal ends 28*c*, both of which may be at the same level, whereas wire loop distal end 28*a* may be slightly below (i.e., proximal to) wire loop distal ends 28*c*. Tube loop distal ends 28*a* may accordingly by slightly above tube loop distal ends 28*b*. Sac 80 may cover the loops and contain dissected tissue.

Figure 2E:
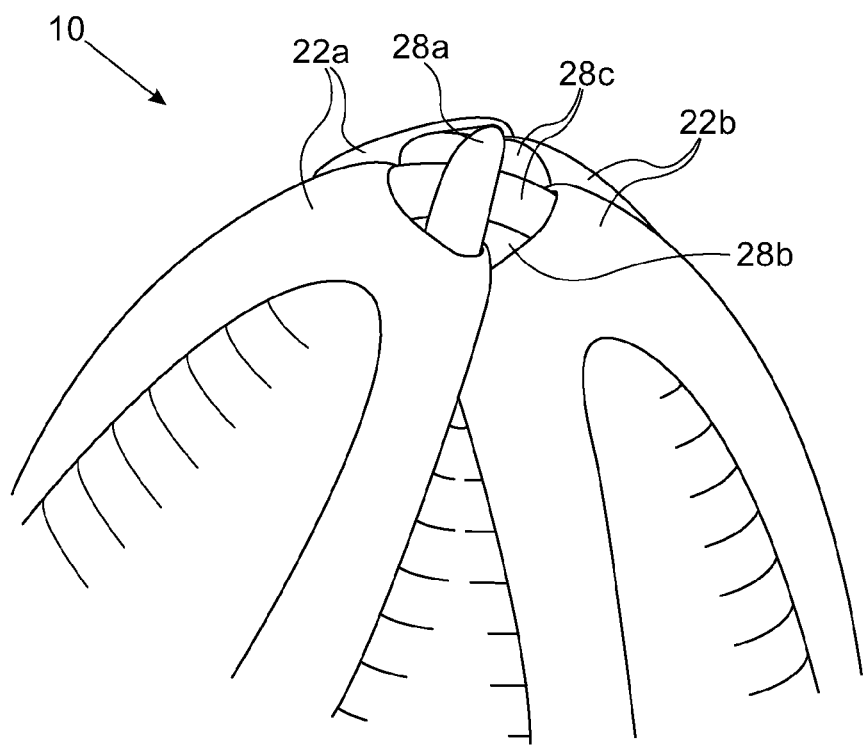
FIG. 2E is a perspective view of a distal end of a tool in a closed state, according to an embodiment of the invention.

FIG. 2E is a perspective view of the distal end of tool 41, closed beyond dissected tissue. More particularly, FIG. 2E is a perspective view of a device 10 with four sets of loops, in its closed state beyond dissected tissue. Tube loop distal ends 22*a* may be slightly above (i.e., distal to) tube loop distal ends 22*b*, with wire loop distal end 28*a* exiting window 23 of tube loop distal ends 22*a*, wire loop distal end 28*b* exiting window 23 of tube loop distal ends 22*b*. Wire loop distal end 28*c* may pass between window 23 of tube loop distal ends 22*a* to window 23 of tube loop distal ends 22*a*.

Wire loops 28*a-c*, create a complete closure of aperture 5. Due to the specific arrangement of wires and loops, wire loop distal end 28*a* may be slightly above (i.e., distal to) two wire loop distal ends 28*c*, both of which may be at the same level, whereas wire loop distal end 28*a* may be slightly below (i.e., proximal to) wire loop distal ends 28*c*. Tube loop distal ends 28*a* may accordingly by slightly above tube loop distal ends 28*b*.

Figure 2F:
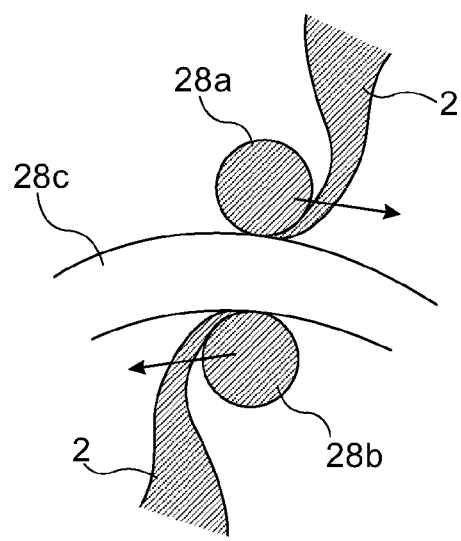
FIG. 2F is a simplified schematic longitudinal cross section through the end of tool showing the scissoring action of the wire loops, according to an embodiment of the invention.

FIG. 2F is a simplified schematic longitudinal cross section through the end of tool 41 showing the scissoring action of the wire loops. More particularly, FIG. 2F is a simplified schematic longitudinal cross section through wire loop distal end 28*c*, in a plain parallel to that created by the arch of wire loop distal end 28*c*. Wire loop distal end 28*a* may be above (distal to) wire loop distal end 28*c*, and wire loop distal end 28*b* may be below (proximal to) wire loop distal end 28*c*. Intima 2, or any other tissue, may be seen trapped between wire distal loop ends 28.

As shown in FIG. 2F, during closure of aperture 5, each of wire loop distal end 28*a* and 28*b* may typically move towards each other and pass each other, scissoring intima 2.

Reference to the term "wire" is mentioned herein, which may refer to any of wires, braided wires or cables, strips, or any other elongate element, having any cross sectional shape, and made of any material.

Reference to the term "tubes" may refer to any elongate hollow element, having any cross sectional profile, and made of any material. The tube loop can be an arch along a longitudinal axis of the sheath in the deployed state. The at least one tube loop can also be an arch having two legs along a longitudinal axis of the sheath in the deployed state. The arch can have a curved symmetrical structure spanning an opening. The arch can be substantially homogeneous and/or seamless such that at least a portion of the surface of the arch is an uninterrupted material. For example, in some embodiments the arch can include a curved tube of a uniform surface with the exception of a distal window.

The at least one wire loop 28 can be a monofilament wire of shape memory material. A shape memory material used in wire loops can be made of a nickel titanium alloy known as nitinol, which is composed of about 55% Ni and 44% Ti, with trace elements of Cu (150 ppm), Fe (110 ppm), and Mn (21 ppm). As a shape memory material, nitinol central wires can have the characteristic of superelasticity whereby they exhibit a superelastic tendency to retain the shape in which they are formed when heat is applied to a suitable presorting temperature. This characteristic serves to reinforce the orientation toward the configuration into which wire loops constructed in this manner are bent. Thus, the at least one wire loop can be a monofilament wire of shape memory material. The at least one wire loop can be made of nitinol.

The use of the composite construction with a nitinol material and surrounding stainless steel strands are also contemplated within broad inventive principles disclosed herein. The composite construction can allow for ease of construction in that the surrounding stainless steel strands can easily be soldered to each other at joints, whereas nitinol material is not nearly so readily joinable. In addition to the improvements in efficiency of construction and enhanced durability and reliability of operation, the use of the described composite construction also provides a savings in cost of material over the use of a single superelastic material for the forming of elastic wires.

It is to be noted that, while specific examples of wire loop composition have been disclosed herein, other configurations are suitable which fall within the scope of this invention.

In an embodiment used for peripheral endarterectomy for the lower limbs, sheath 12 may be preferably made of a flexible polymer with relatively high axial strength such as PEBAX or PEEK etc., with an outer diameter of approximately 3.4 mm and a wall thickness of 0.1 mm, and a length of approximately 120-160 cm. Atraumatic tip 17 may be made of a softer material as known in the art. Tube loops 14 may preferably be made of a resilient material such as a stainless steel braid, e.g. HHS® tube from Fort Wayne metals, having a small outer diameter of approximately 0.014" and wall thickness of approximately 0.0019". Wires 24 may preferably be resilient wires or cables such as nitinol, stainless steel etc., with an OD of approximately 0.0078".

For peripheral endarterectomy of the lower limbs, distance D may typically be 10-40 cm, preferably 20-30 cm.

For carotid endarterectomy, distance D may typically be 5-15 cm, preferably 8-12 cm.

For coronary endarterectomy, distance D may typically be 0.5-10 cm, preferably 1-3 cm. The device can be configured for the minimally invasive removal of tissue in an endarterectomy.

Of note, windows 23 may have a length, which is typically 0.5-5 times the diameter of tube loops 18, preferably 0.8-3 times this diameter. A smaller diameter might cause excessive friction between wires, a larger diameter interferes with complete closure of aperture 5.

Each window 23 may be a longitudinal slot as depicted in FIGS. 1A and 1B, or may alternatively consist of two separate holes or openings in tube loop distal end 22, in which case the window length mentioned above would refer to the distance between these openings.

Using tube loops 18 as part of the design is beneficial in several ways, as opposed to using a separate tube for each leg of wire loops 24.

First, the tube loops provide support for the combined tube-wire structure which forms aperture 5. If tube loops are disconnected into separate tubes, the structure loses its stability and typically flattens out.

Second, during advancement of device 10 for dissection of the plaque, tube loops act as springs, which store energy when pushed from the proximal end, and then release it, propelling the distal end of the device further along the lesion.

Third, the tubes themselves provide support to the excised tissue during removal from the body. Loops create closer pairs of tubes that provide better support.

FIGS. 3A-3H describe the stages of a procedure using device 10.

All of FIGS. 3A-3H are simplified schematic longitudinal sections of a hollow body organ, in which device 10 is seen in side view. In all these figures, wall 1 of hollow body organ is seen, covered by an internal layer 2, and having lumen 3 blocked by blockage 4. Guiding catheter 6 is seen at the proximal end of the hollow body organ.

In the case that the described procedure is a percutaneous remote endarterectomy, the hollow body organ may be an artery, wall 1 may consist of the media and adventitia of the artery, layer 2 may be the intimal layer, and blockage 4 may be an atherosclerotic lesion.

Figure 3A:
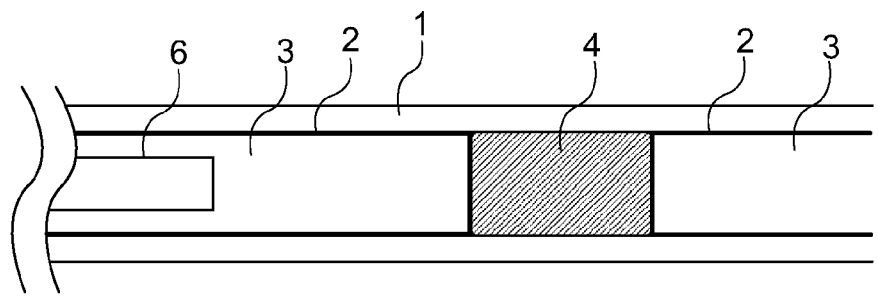
FIG. 3A shows the site of an intended procedure just before insertion of device, according to an embodiment of the invention.

More particularly, FIG. 3A shows the site of an intended procedure just before insertion of device 10. A guiding catheter 6 is shown in lumen 3, proximal to blockage 4, optionally having been placed under fluoroscopic guidance or using other imaging modalities.

Figure 3B:
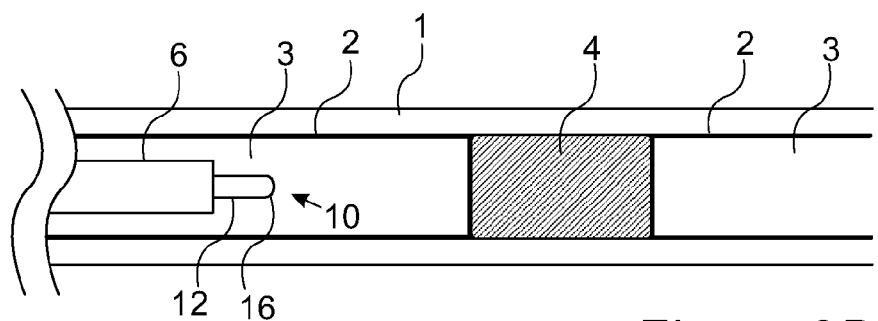
FIG. 3B shows the site of an intended procedure just after insertion of device, according to an embodiment of the invention.

FIG. 3B shows the site of an intended procedure just after insertion of device 10 through guiding catheter 6, including the same features and components shown in FIG. 3A. In addition, sheath 12 of device 10 is seen protruding distally out of guiding catheter 6, proximal to blockage 4. Distal end 16 of sheath 12 is distal to guiding catheter 6 and proximal to blockage 4.

Note that use of guiding catheter 6 is optional. Device 10 may be inserted over a wire, or even without either a wire or a guiding catheter.

In FIG. 3B, device 10 is seen in its initial/basic state, with tool 41 still inside sheath 12.

Figure 3C:
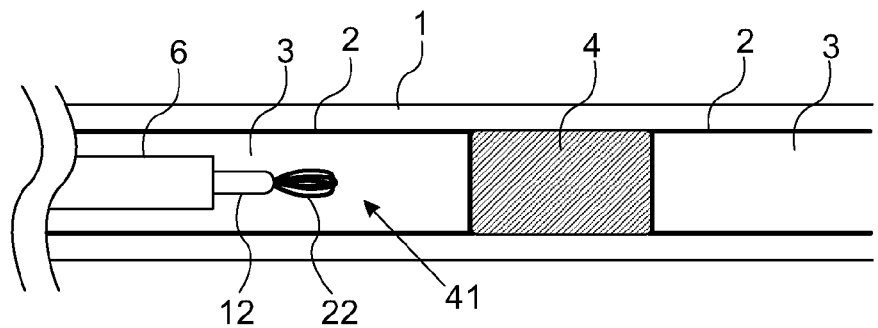
FIG. 3C shows the site of a procedure during deployment of device, according to an embodiment of the invention.

FIG. 3C shows the site of a procedure during passage of tool 41 out of sheath 12, including the same features and components shown in FIG. 3B. In addition, tube loop distal ends 22 are seen protruding distally out of sheath 12, still proximal to blockage 4.

In FIG. 3C, tool 41 is still crimped, i.e., tube loop distal ends 22 are seen protruding out of sheath 12, however wire loop ends 28 have not yet pushed out, and aperture 5 has not yet expanded.

Figure 3D:
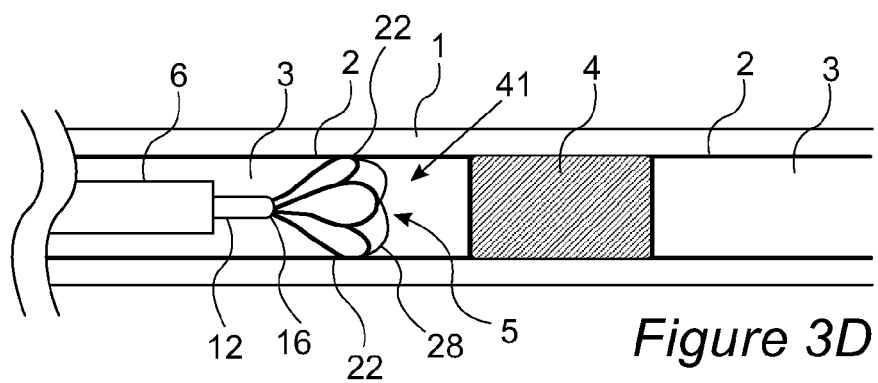
FIG. 3D shows the site of a procedure at the end of expansion of aperture of device, according to an embodiment of the invention.

FIG. 3D shows the site of a procedure at the end of deployment, including the same features and components shown in FIG. 3B. In addition, tube loop distal ends 22 are seen protruding distally out of sheath 12, and wire loop distal ends 28 are seen protruding distally out of tube loop distal ends 22, still proximal to blockage 4.

In FIG. 3D, device 10 is seen in its deployed state, tube loop distal ends 22 are seen protruding out of sheath 12 and radially expanded, wire loop ends 28 are seen protruding out of tube loop distal ends 22 and radially expanded, and aperture 5 is fully expanded, such that tube loop distal ends 22 and wire loop distal ends 28 are in contact with wall 1.

Figure 3E:
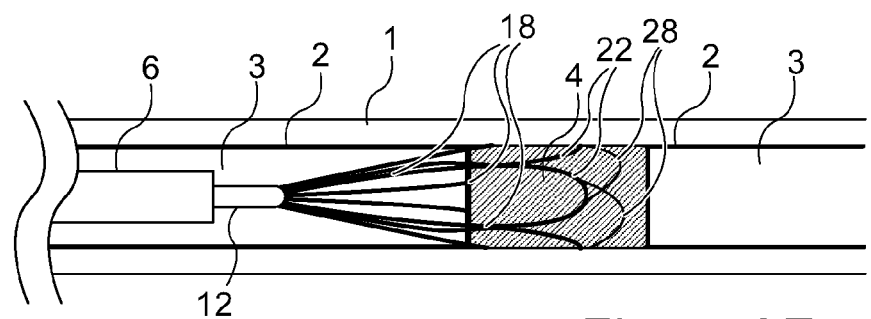
FIG. 3E shows the site of a procedure following expansion of aperture and during advancement of device, according to an embodiment of the invention.

FIG. 3E shows the site of a procedure following deployment and during advancement of device 10, including the same features and components shown in FIG. 3B. In addition, tube loop distal ends 22 are seen protruding distally out of sheath 12, and wire loop distal ends 28 are seen protruding distally out of tube loop distal ends 22, now passing between blockage 4 and wall 1. In an endarterectomy procedure, loops would now be within the subintimal space.

In FIG. 3E, device 10 is seen in its deployed state, tube loop distal ends 22 are seen protruding out of sheath 12, radially expanded, and passing along and around blockage 4. Wire loop ends 28 are seen protruding out of tube loop distal ends 22 and radially expanded, being advanced distally by the user, and passing around and along blockage 4.

Figure 3F:
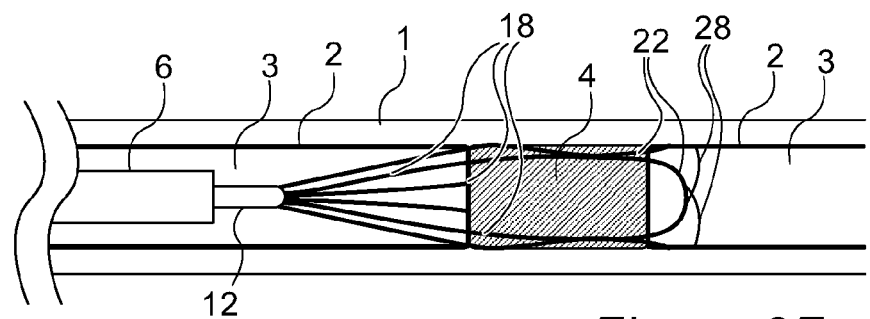
FIG. 3F shows the site of a procedure following advancement of device beyond blockage, according to an embodiment of the invention.

FIG. 3F shows the site of a procedure following advancement of device 10 beyond blockage 4, including the same features and components shown in FIG. 3B. In addition, tube loops 18 are seen protruding distally out of sheath 12, and wire loop distal ends 28 are seen protruding distally out of tube loop distal ends 22, having passed between blockage 4 and wall 1.

In FIG. 3F, device 10 is seen still in its deployed state, tube loops 18 are seen protruding out of sheath 12, radially expanded, and having been advanced along and around blockage 4, beyond its distal end. Wire loop distal ends 28 are seen protruding out of tube loop distal ends 22 and radially expanded, and passing around and along blockage 4, beyond its distal end.

FIG. 3F shows that device 10 has now traversed blockage 4.

Figure 3G:
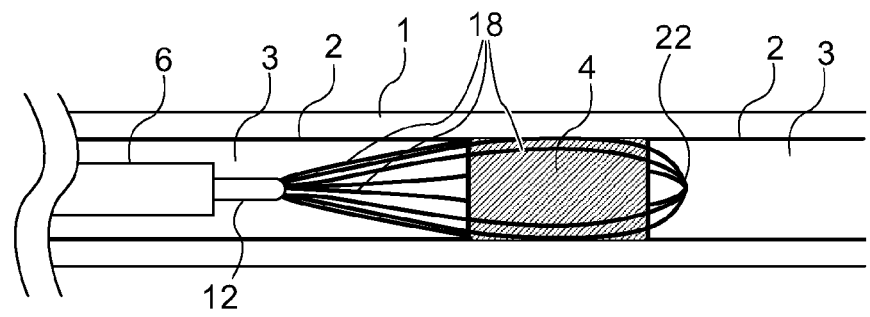
FIG. 3G shows the site of a procedure following closure of device beyond blockage, according to an embodiment of the invention.

FIG. 3G shows the site of a procedure following closure of device 10 beyond blockage 4, including the same features and components shown in FIG. 3B. In addition, tube loops 18 are seen protruding distally out of sheath 12, expanding radially, passing along blockage 4, and coalescing distal to it.

In FIG. 3G, device 10 is seen in its closed state, tube loops 18 are seen protruding out of sheath 12, radially expanded, and passing along and around blockage 4, then joining together beyond its distal end. Wire loop distal ends 28 are not seen as they were pulled back into tube loop distal ends 22 in order to close aperture 5, which is now closed.

Figure 3H:
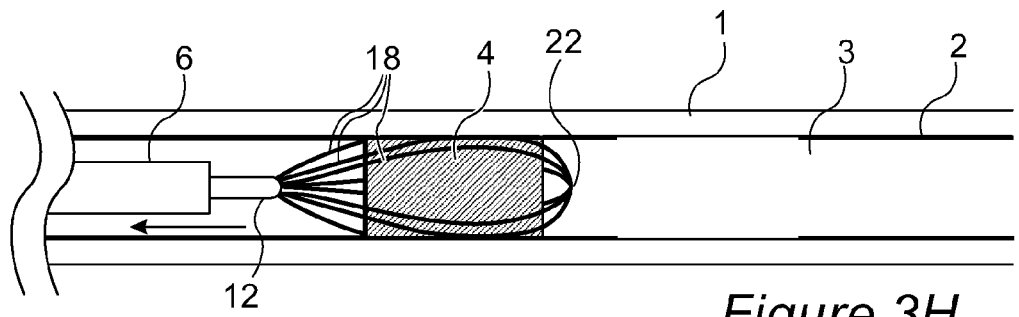
FIG. 3H shows the site of a procedure during removal of device containing blockage tissue, according to an embodiment of the invention.

FIG. 3H shows the site of a procedure during removal of device 10, including the same features and components shown in FIG. 3B. In addition, tube loops 18 are seen protruding distally out of sheath 12, expanding radially, passing along blockage 4, and coalescing distal to it.

In FIG. 3H, device 10 is seen in its closed state, tube loops 18 are seen protruding out of sheath 12, radially expanded, and passing along and around blockage 4, then joining together beyond its distal end. Wire loop distal ends 28 are not seen as they were pulled back into tube loop distal ends 22 in order to close aperture 5, which is now closed.

In FIG. 3H, device 10 in its closed state containing blockage 4 or any excised tissue is seen being pulled proximally. Device 10 may subsequently be removed from the body through the percutaneous entry site.

Not shown (for clarity) is sac 80, which can contain blockage 4 by the end of the procedure. FIGS. 4A-4F are schematic front views of device 10 showing various configurations of wires and tubes in accordance with the current invention. In the following description, the terms "clockwise" and "counter-clockwise" refer to directions relative to the center of FIG. 4A, for example, from a distal end perspective.

As can be seen from FIGS. 4A-4F, the at least one tube loop 18 can have a window 23 that allows for passage of the at least one wire loop 28. In some embodiments, the window of the at least one tube loop can be a distal window. That is, the tube loop can have the window at the distal end of the tube loop. The at least one tube loop can be hollow to surround the at least one wire loop in the crimped state. The wire loop can be exit-able and/or extendable from the at least one tube loop. A diameter of the at least one wire loop can be less than an inner diameter of the at least one tube loop. Typically the diameter of the at least one wire loop will be in close fit to the inner diameter of the at least one tube loop.

The window can have a longitudinal axis. The at least one tube loop can have a longitudinal axis, and the distal window can have a length along the longitudinal axis in a range between about 0.5 to about 5 times a diameter of the at least one tube loop. In some embodiments, the distal window can have a length along the longitudinal axis of a range between about 0.8 to about 3 times a diameter of the tube loop.

Figure 4A:
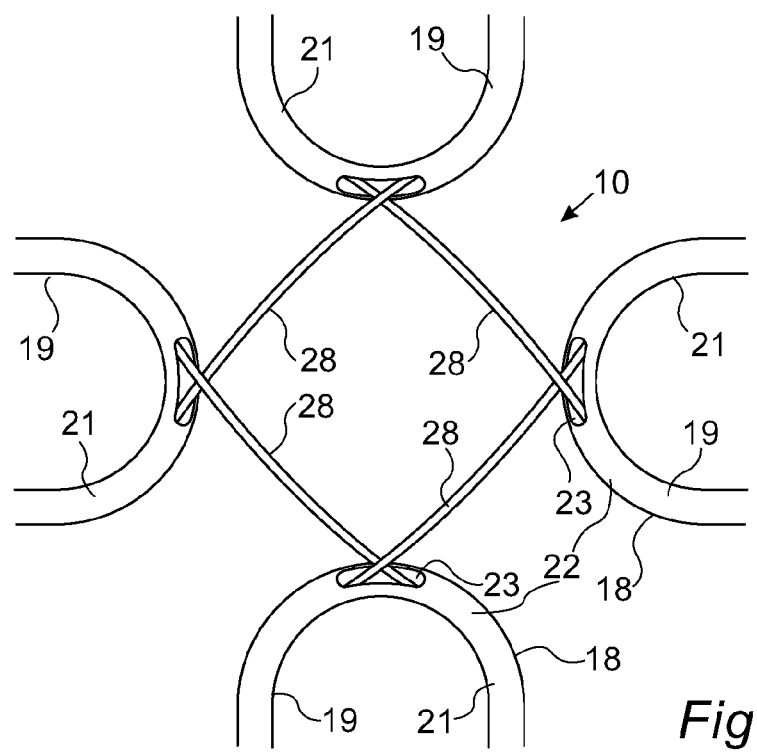
FIG. 4a shows a schematic distal-end view of loops of the device, according to an embodiment of the invention.

More particularly, FIG. 4A is a schematic front view of the tip of device 10 with four tube loops 18 having distal ends 22 and windows 23, each tube loop 18 having a "clockwise" oriented leg 19 and a "counter-clockwise" oriented leg 21. As can be seen, the at least one tube loop can include four spatially equidistant loops.

Wire loop distal ends 28 are shown, each with a "counter-clockwise" leg threaded through window 23 and leg 21 of one tube loop 18, and a "clockwise" leg threaded through window 23 and leg 19 of another tube loop 18, located adjacent to previous loop 18 in a clockwise direction.

Each "counter-clockwise" leg of wire loop distal end 28 passes below adjacent wire loop distal end 28 when entering leg 21, and each "clockwise" leg of wire loop distal end 28 passes above adjacent wire loop distal end 28 when entering leg 19, such that each wire loop distal end 28 spans between the two most distant legs 21 and 19 of two adjacent tube loops 18. Thus, each tube loop can have a first and a second wire loop. From a distal end view in the radial axis of the sheath, the second wire loop can extend under the first wire loop in a clockwise direction of the radial axis of the sheath. Thus, in this embodiment, each of a first set of two opposing wire loops extends over one of a second set of opposing wire loops that are adjacent to the first set. Further, each of the second set of opposing wire loops can extend under one of the first set of opposing wire loops in a radial axis of the sheath.

Figure 4B:
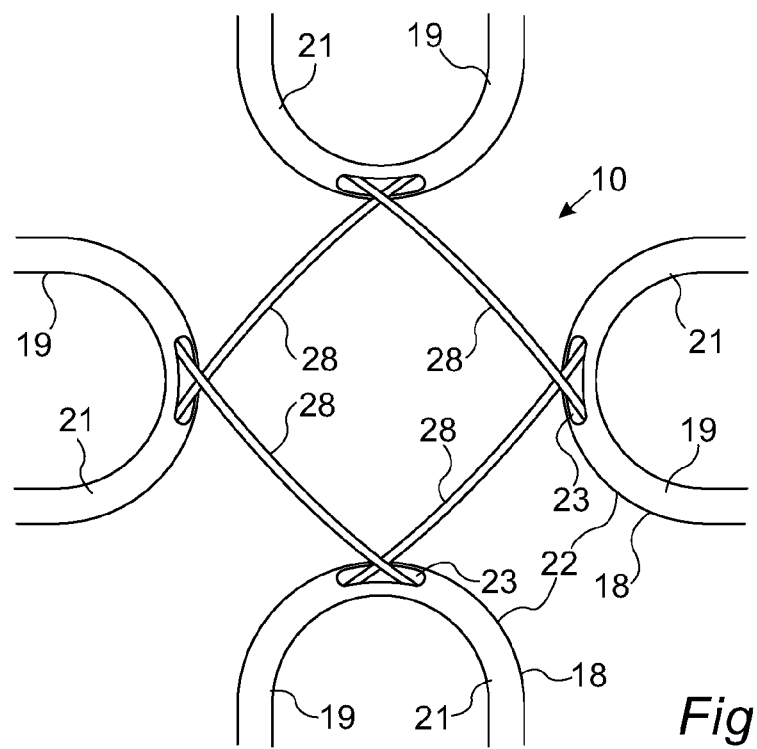
FIG. 4B shows a schematic distal-end view of loops of the device, according to an embodiment of the invention.

FIG. 4B describes another preferred embodiment with a different arrangement of wires.

More particularly, FIG. 4B is a schematic front view of the tip of device 10 showing the same features as FIG. 4A, except that in this embodiment, two opposing wire loop distal ends 28 pass only above adjacent wire loop distal ends 28. Thus, in this embodiment each of a first set of opposing wire loops extends over both of a second set of opposing wire loops that are adjacent to the first set. Further, each of the second set of opposing wire loops extends under the first set of adjacent opposing wire loops in a radial axis of the sheath.

Figure 4C:
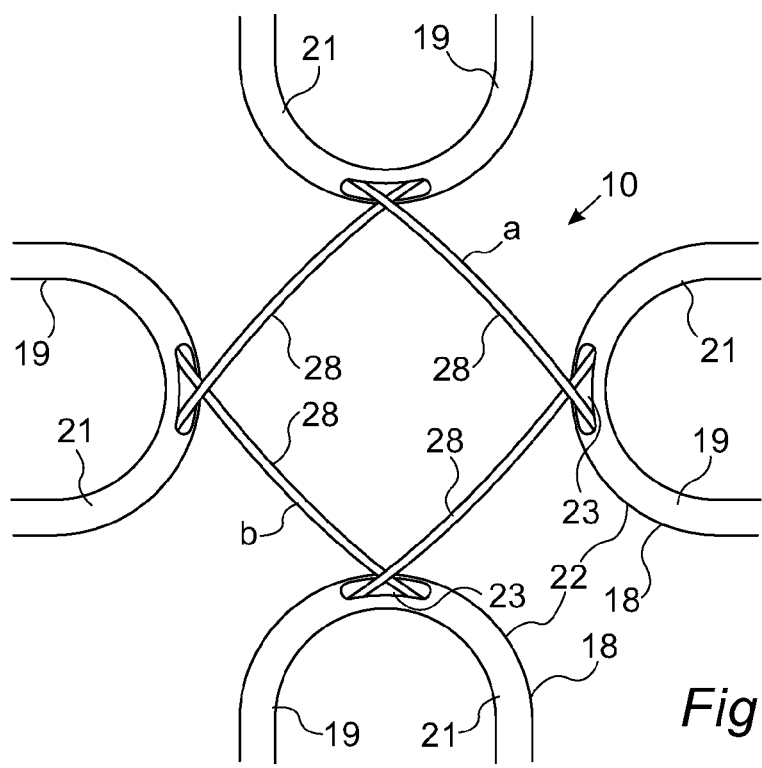
FIG. 4C shows a schematic distal-end view of loops of the device, according to an embodiment of the invention.

FIG. 4C describes yet another embodiment with a different arrangement of wires.

More particularly, FIG. 4C is a schematic front view of the tip of device 10 showing the same features as FIG. 4A, except that in this embodiment, one wire loop distal end 28 (marked a in FIG. 4C) passes only above adjacent wires, and the opposing wire loop distal end 28 (marked b in FIG. 4C) passes only below adjacent wire loop ends 28. In this embodiment, one wire loop can extend over adjacent wire loops and an opposing wire loop can extend under adjacent wire loops.

Figure 4D:
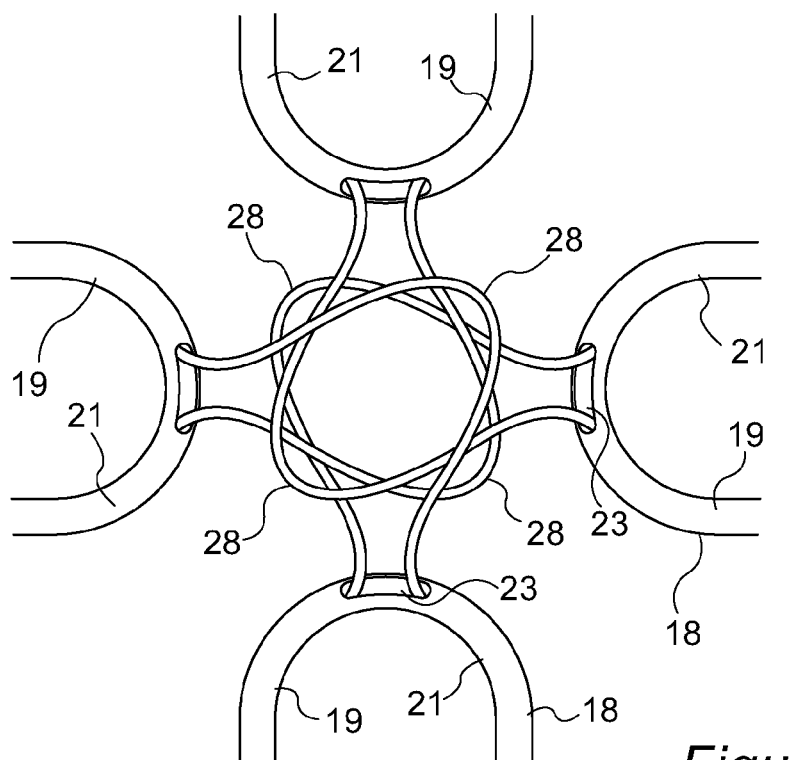
FIG. 4D shows a schematic distal-end view of loops having bends in the cross-section of the device, according to an embodiment of the invention.

FIG. 4D describes yet another embodiment with a different arrangement of wires.

More particularly, FIG. 4D is a schematic front view of the tip of device 10 showing the same features as FIG. 4A, except that in this embodiment, each wire loop distal end 28 passes to the side of the catheter opposite from where it exits window 23, such that when tube loops 18 are advanced into the blood vessel, each said wire loop end 18 remains adjacent the opposite side of the vessel. When the wires are pulled back, each wire passes across the center line of the vessel, thus creating a scissoring action and ensuring the intima is cut. In this embodiment the wires do not cross each other (i.e. are not interlaced). Each wire loop can have a pre-formed curvature around a radial axis of the sheath. The curvature can be radially displaced from a longitudinal axis of the sheath. At least one of the wire loops can extend over at least another wire loop and at least one of the wire loops can extend under at least another of the wire loops in the radial axis of the sheath.

The wire loops can be moveable to a plurality of locations with respect to a radial axis of the sheath. The wire loops can be configured to contact each other. The wire loops can be configured to close such that a scissor action between adjacent wires is operable to cut intima of the tissue. In a radial axis of the sheath, each wire loop can extend under another wire loop and over another wire loop.

Figure 4E:
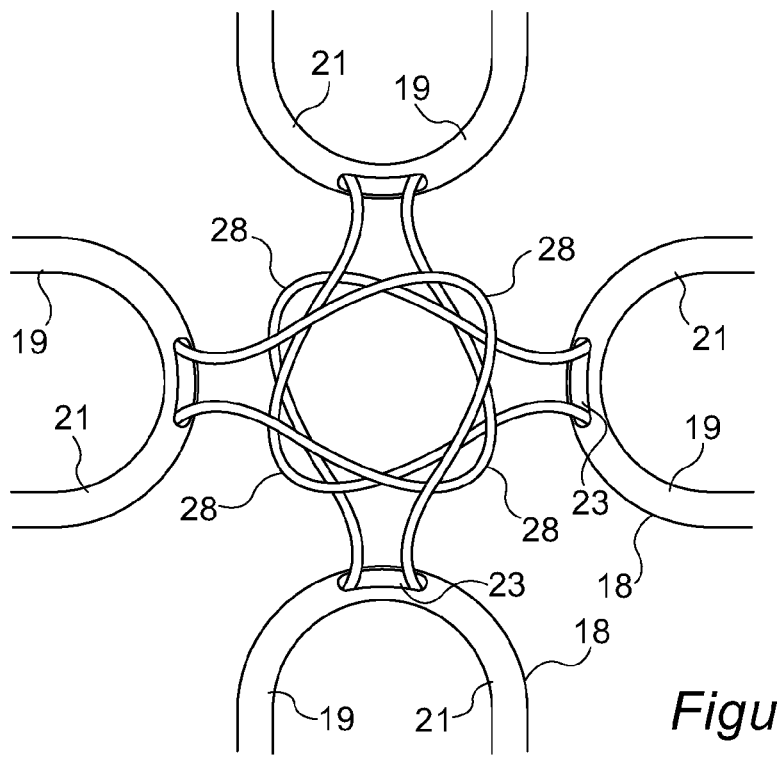
FIG. 4E shows a schematic distal-end view of loops having bends in the cross-section of the device, according to an embodiment of the invention.

FIG. 4E describes yet another embodiment with a different arrangement of wires.

More particularly, FIG. 4E is a schematic front view of the tip of device 10 showing the same features as FIG. 4D, except that in this embodiment, three of the wires are interlaced with adjacent wires. Only the top (i.e. most distal) wire is above all others and not interlaced with any of them. This enables the wires to pass the center line of the vessel when they are pulled, creating a scissoring action between adjacent wires, ensuring the intima is cut. Thus, as can be seen from FIG. 4E, a first wire loop can extend over all other wire loops and other wire loops can be interlaced with adjacent wire loops in the radial axis of the sheath. The first wire loop when retracted can be configured to pass a center line of the body lumen. Each expandable loop can have a first wire loop that extends in a counter-clockwise direction of the radial axis of the sheath and a second wire loop that extends in a clockwise direction of the radial axis of the sheath. As shown in FIG. 4E, the first and second wire loops can cross each other in the radial axis.

Figure 4F:
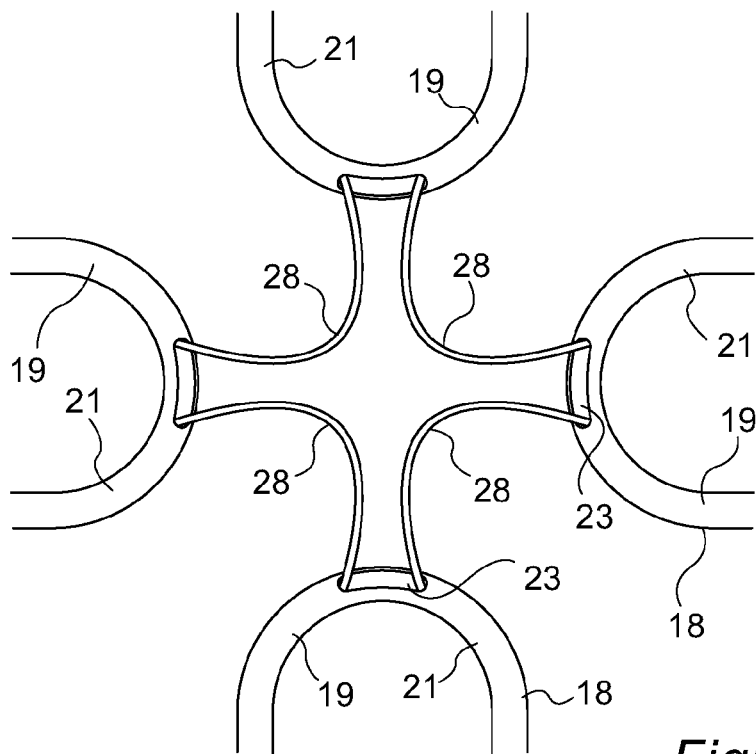
FIG. 4F shows a schematic distal-end view of loops having bends in the cross-section of the device, according to an embodiment of the invention.

FIG. 4F describes yet another embodiment with a different arrangement of wires.

More particularly, FIG. 4F is a schematic front view of the tip of device 10 showing the same features as FIG. 4A, except that in this embodiment, each wire loop distal end 28 has a "counter-clockwise" leg threaded through window 23 and leg 19 of one tube loop 18, and a "clockwise" free end threaded through window 23 and leg 21 of another tube loop 18, located adjacent to previous loop 18 in a clockwise direction. In this configuration each wire loop end spans between the two closest legs 21 and 19 of two adjacent tube loops 18, such that no wires cross one over the other. In this embodiment, the first and second wire loops do not cross each other in the radial axis.

In practice, this configuration tends to naturally flip into a configuration similar to that in FIG. 4A, unless tube loop ends 22 are intentionally kept in this orientation, for example by a multilumen tube or other techniques as further described below.

Various other wire and tube configurations are possible and are included in the scope of this invention.

Although in the embodiments described above, all of wire loops 24, or all of tube loops 18 are typically advanced together as one, in other embodiments, each wire loop 24 or tube loop 18 can be advanced individually. This may provide greater control over the stages of separation of the plaque. Optionally, wires can be operated in groups, e.g. one group comprising two wires having wire loops distal ends 28 running in parallel, and the other group comprising the two other wires having wire loops distal ends 28 perpendicular to them. Alternatively one group may comprise three wires, while the other group comprises the fourth wire. Clearly, many different combinations exist, especially if more than four loops are used.

Although in the embodiments described above, wire loops 24 are typically advanced by advancing both proximal ends 26 of wire loop 24, in other embodiments one proximal end 26 is kept fixed in relation to sheath 12, while only the other proximal end 26 of the same wire loop 24 is advanced, such that wire loop distal end 28 of wire loop 24 is formed of a different segment of wire loop 24 at each given moment. This may be achieved for example by one proximal wire loop end 26 being attached to tube loop 18 a short distance (e.g. 1-5 cm) proximal to tube loop distal end 22. An advantage is that while in the previously described embodiments, the segment of wire loop 24 forming the bend at wire loop distal end 28 might apply relatively low radial force when opening aperture 5, according to the current embodiment, a new, unbent segment of wire is pushed distally to form wire loop distal end 28, and will therefore have greater radial force.

Figure 4G:
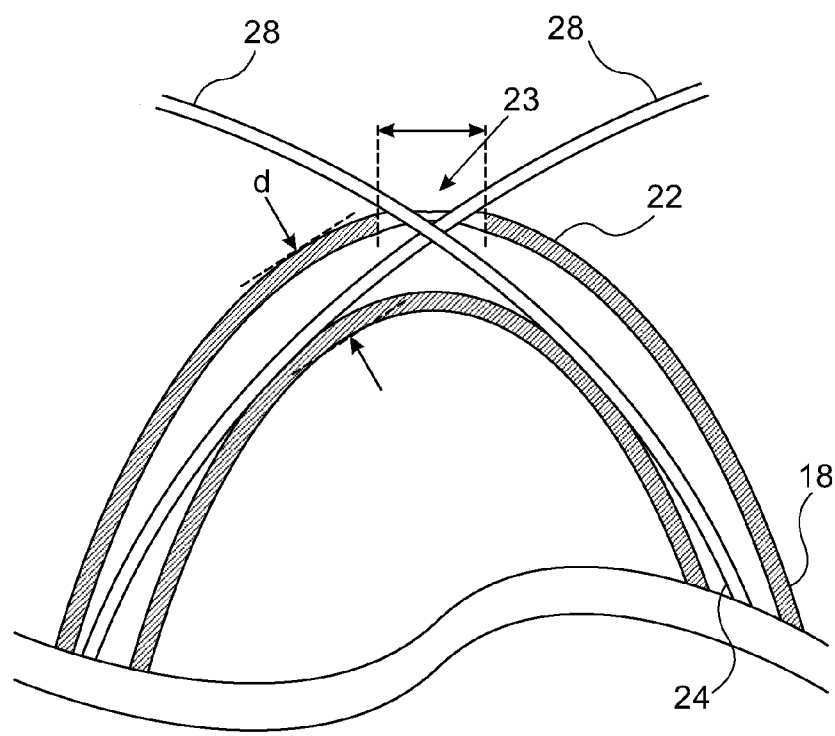
FIG. 4G depicts a window of a tube loop as a single slot, according to an embodiment of the invention.

FIG. 4G shows an embodiment in which window 23 consists of a single elongate slot.

More particularly, FIG. 4G is a schematic cross section of tube loop distal end 22 showing wire loops 24 passing through it and exiting its distal end through window 23. Window 23 has a length 1. Typically, wire loop distal ends 28 will exit tube loop distal end 22 at the two lateral edges of window 23. Tube loop distal end 22 has a diameter d.

Figure 4H:
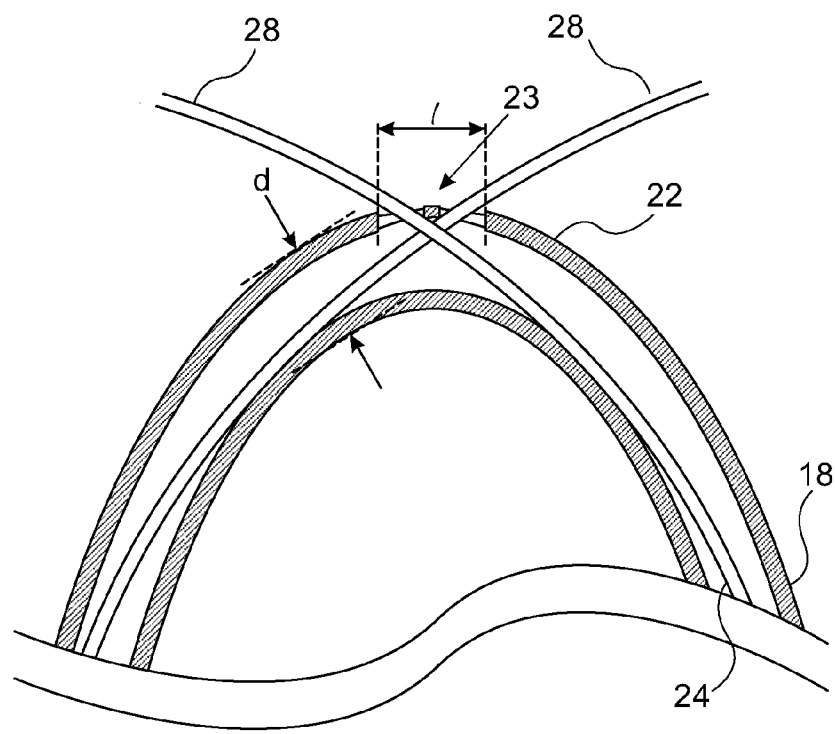
FIG. 4H shows a window including two discrete holes, according to an embodiment of the invention.

FIG. 4H shows an embodiment in which window 23 consists of two discrete holes or openings. Thus, the window 23 of the at least one tube loop can be a distal window. That is, the window can be disposed at a distal position of the tube loop. Further, the window can outline two holes or openings. In this embodiment, the two holes can house two wire loops, for example. More particularly, FIG. 4H is a schematic cross section of tube loop distal end 22 showing wire loops 24 passing through it and exiting its distal end through a window 23 consisting of two separate holes. In this embodiment, 1 indicates the distance between the farthest ends of the two holes. Tube loop distal end 22 has a diameter d.

Of note, these are schematic drawings, which do not depict the exact relationship between components. Typically, the inner diameter of tube loops 18 would closely match the outer diameter of wires 24.

One of the goals of the current invention is to provide means for cutting the tissue at the distal end of the dissected lesion, as an integral part of the same percutaneous device used for dissection around the lesion. FIGS. 5-6 describe examples of such means.

In an embodiment shown in FIG. 5, the inner side (the side far from the vessel wall) of at least one of windows 23 of tube loop end 22 has a sharp edge or element 60, configured to cut intima or plaque.

More particularly, FIG. 5 is a perspective view of tube loop distal end 22 of device 10, showing two legs of wire loop distal ends 28 exiting window 23. Sharp element 60 may consist of a sharpened edge of window 23 of tube loop distal end 28. Typically, element 60 is located at the lumen side of window 23, so it does not contact the vessel wall.

Optionally, element 60 is capable of transitioning between a sharp and blunt state, for example, by changing its orientation relative to the longitudinal axis of tube loop distal ends 22. The sharp and blunt state can also be a cutting and non-cutting state, respectively. In an embodiment, this transition is achieved by the tightening of wire loops 24 during closure of aperture 5 of device 10. When the user wishes to excise the lesion, wires 24 are pulled back, bringing sharp element 60 in contact with the outer side of the intima, and cutting it, even if it is thickened and hardened due to disease.

Figure 5A:
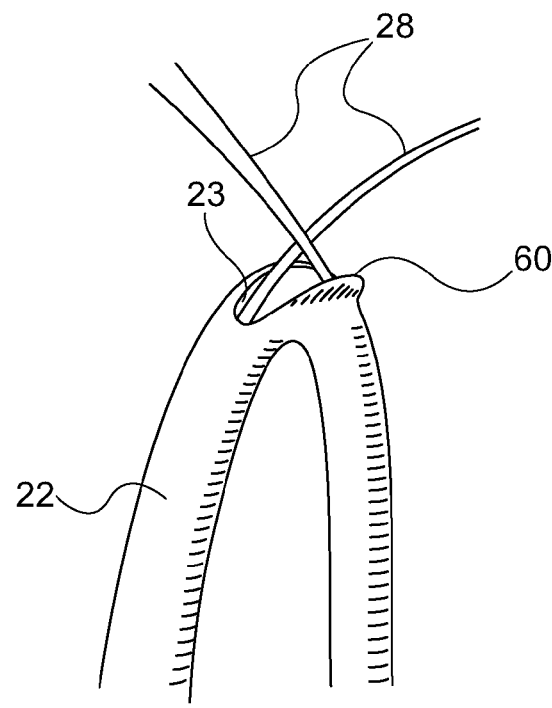
FIG. 5A shows a close-up perspective view of wire loops coming from a tube loop, according to an embodiment of the invention.
Figure 5B:
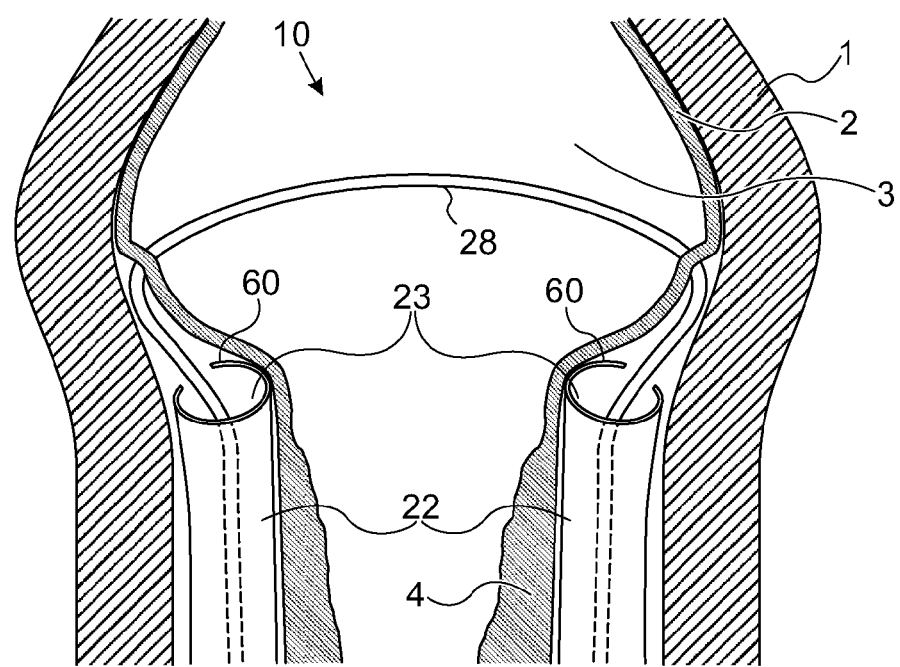
FIG. 5B shows a cross section side view of the tip of a device in a deployed state inside an artery at the distal end of a lesion, according to an embodiment of the invention.
Figure 5C:
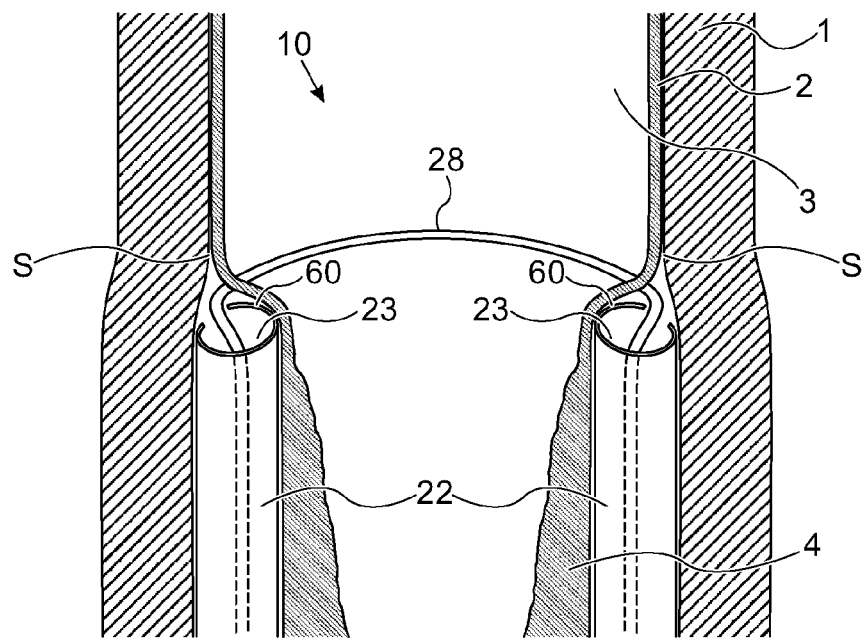
FIG. 5C shows a cross section side view of the tip of a device in a less deployed state than FIG. 5B inside an artery at the distal end of a lesion, according to an embodiment of the invention.
Figure 5D:
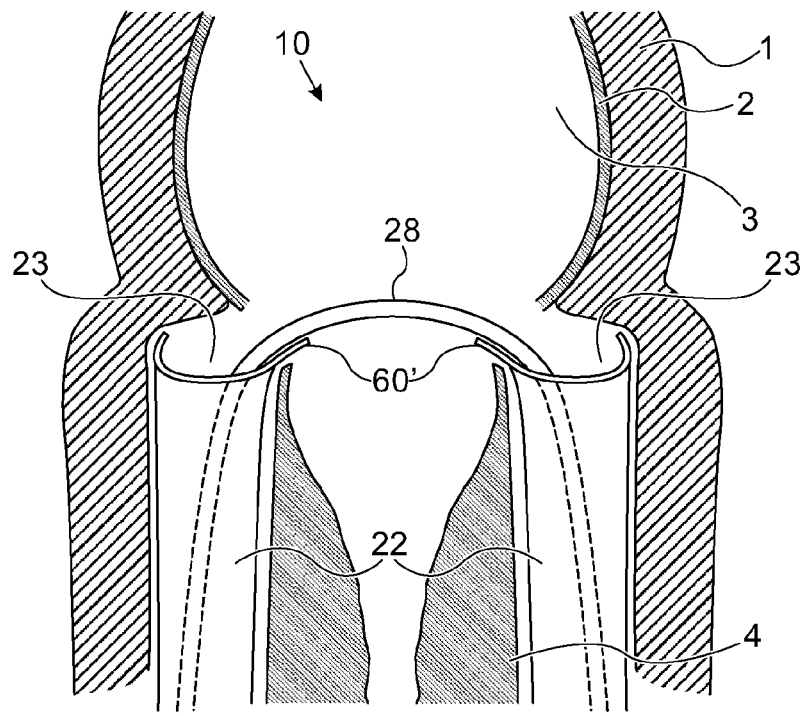
FIG. 5D shows a cross section side view of the tip of a device in a less deployed state than FIGS. 5B and 5C inside an artery at the distal end of a lesion, according to an embodiment of the invention.

Use of this embodiment is depicted in FIGS. 5B-5D.

FIG. 5B depicts the situation before beginning the cutting stage, FIG. 5C is a "snapshot" of the situation during the cutting stage, just before the transition of sharp elements 60 to their sharp state, and FIG. 5D is a "snapshot" of the situation at the moment of cutting the intima, just after sharp elements 60 have transitioned to their sharp state. Thus, the at least one tube loop can include a sharp element at the distal end. The distal end of the at least one tube loop can include a blunt portion that is oriented away from an arterial wall of the body lumen and can include a sharp portion having the sharp element that protrudes into the tissue to be removed.

A detailed explanation of the cutting process follows:

FIG. 5B is a simplified schematic longitudinal cross section—side view of the tip of device 10 in its deployed state, inside an artery at the distal end of an atherosclerotic lesion, with sharp elements 60 in their blunt state. This Fig. depicts the situation at the end of the procedure, just before cutting the end of the lesion.

More particularly, arterial wall 1 is shown with its intimal layer 2 and arterial lumen 3. Inside arterial lumen 3, the tip of device 10 is seen comprising tube loop distal ends 22 shown with the plane of section passing through their middle. Wire loop distal ends 28 are seen protruding outwardly through windows 23, extending radially and engaging arterial wall 1, thus dissecting within the subintimal space, between arterial wall 1 and intimal layer 2, and separating plaque 4 seen at a more proximal location inside device 10. For the sake of clarity, only two tube loop distal ends 22, and two wire loop distal ends 28, are shown, although the device may consist of any number of these.

Sharp elements 60 are seen at the luminal side of windows 23, coiled towards their lateral side. Sharp elements 60 do not engage the arterial wall because they do not protrude beyond the lateral edge of window 23, and also because wire loop distal ends 28 push arterial wall 1 outwardly. Thus sharp elements 60 do not interfere with dissection.

FIG. 5C is a simplified schematic longitudinal cross section—side view of the tip of device 10 in its semi-deployed state (or during transition from its deployed state to its closed state), inside an artery at the distal end of an atherosclerotic lesion, with sharp elements 60 still in their blunt state. This figure depicts the situation during beginning of closure of aperture 5, just before cutting the end of the lesion.

More particularly, arterial wall 1 is shown with its intimal layer 2 and arterial lumen 3. Inside arterial lumen 3, the tip of device 10 is seen comprising tube loop distal ends 22 shown with the plane of section passing through their middle. Wire loop distal ends 28 are seen protruding outwardly through windows 23, engaging arterial wall 1 but not pushing it radially.

At this stage, wire loop distal ends 28 were drawn proximally just enough to not protrude radially beyond tube loop distal ends 22, and the device was advanced slightly distally, so that points S, where intimal layer 2 separates from arterial wall 1 are as close as possible to sharp elements 60. This is done in order to minimize the length of any intimal flap that might be created.

For the sake of clarity, only two tube loop distal ends 22, and two wire loop distal ends 28, are shown, although the device may consist of any number of these.

Sharp elements 60 are seen at the luminal side of windows 23, coiled towards their lateral side. Sharp elements 60 do not engage the arterial wall because they do not protrude beyond the lateral edge of window 23.

FIG. 5D is a simplified schematic longitudinal cross section—side view of the tip of device 10 in its almost closed state (or towards the end of transition from its deployed state to its closed state), inside an artery at the distal end of an atherosclerotic lesion, with sharp elements 60 now in their sharp state. This figure depicts the situation during closure of aperture 5, just at the moment of cutting the end of the lesion.

More particularly, arterial wall 1 is shown with its intimal layer 2 and arterial lumen 3. Inside arterial lumen 3, the tip of device 10 is seen comprising tube loop distal ends 22 shown with the plane of section passing through their middle. Wire loop distal ends 28 are seen exiting through windows 23, pulling tube loop distal ends 22 towards each other. At this stage, wire loop distal ends 28 were drawn further proximally, applying tension between tube loop distal ends 22, and applying force on sharp elements 60', which have now transitioned to their sharp state facing the luminal side and have cut intimal layer 2.

For the sake of clarity, only two tube loop distal ends 22, and two wire loop distal ends 28, are shown, although the device may consist of any number of these.

Sharp elements 60 are seen at the luminal side of windows 23, now facing the luminal side.

Note that arterial wall 1 is depicted kinked at the cutting point. This kink may occur temporarily during the cutting stage due to the inward forces applied by the loops and sharp elements which pull the intima and arterial wall, but may resolve immediately once the intima has been cut.

In another embodiment, the inner edge of wire loop distal ends 28 is made sharp, thus enhancing cutting capability.

In another embodiment shown in FIGS. 6A-6D, a cutting element is positioned around the tip of device 10 so that at the end of the procedure it is ideally located to cut the tissue at a point beyond the dissected lesion.

Cutting element 70 may be a thin but durable wire, a strip which is at least slightly sharp in the area of wire loop distal ends 28, or any element configured for cutting tissue such as a resistor which heats upon transfer of electrical current through it, an optic fiber delivering laser light, or any other appropriate cutting elements as known in the art.

FIGS. 6A-6D describe the cutting process using cutting element 70. For the sake of clarity, only three tube loop distal ends 22 and wire loop distal ends 28 are shown, the artery is not shown, and in FIGS. 6A, 6C, and 6D, wire loop distal ends 28 are not shown. Also for the sake of clarity, the cutting stage is depicted as if occurring very close to sheath 12, whereas in practice this is typically done at a significant distance from the sheath.

Figure 6A:
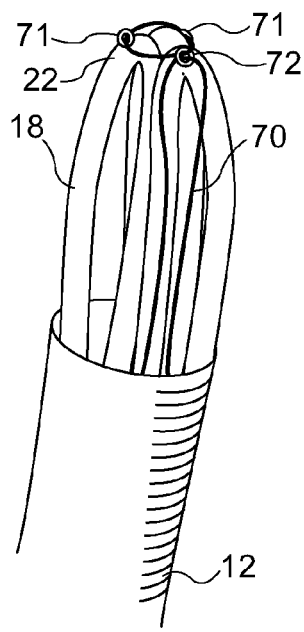
FIG. 6A shows a perspective view of a distal end of a device with a cutting element in a deployed state, according to an embodiment of the invention.
Figure 6B:
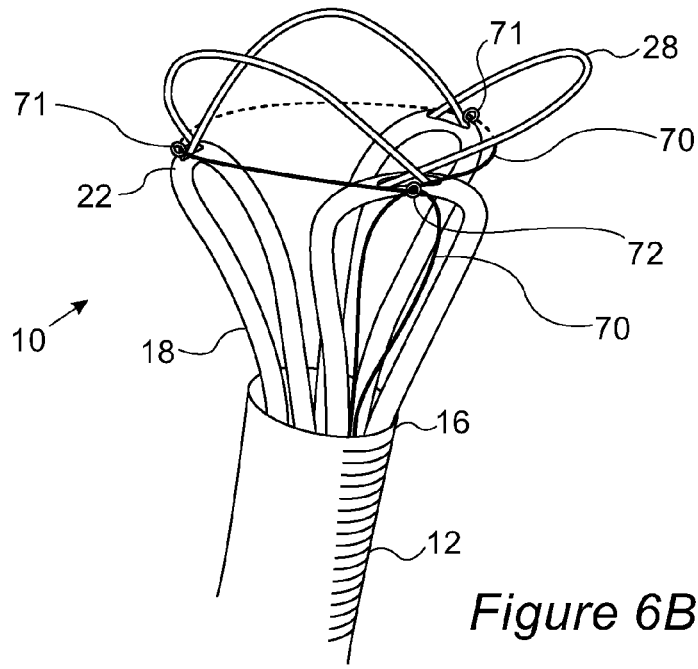
FIG. 6B shows the device of FIG. 6A in an expanded state, according to an embodiment of the invention.

FIG. 6A is a 3D depiction of the tip of device 10 in its crimped state. Thus, the device can further include a cutting element that is located at the distal end of the at least one tube loop. The cutting element can be configured to expand radially with expansion of the aperture, as shown in FIG. 6B. The cutting element can surround the aperture of the tool.

FIG. 6B is a 3D depiction of the tip of device 10 in its deployed state.

More particularly, distal end 16 of sheath 12 of device 10 is seen, from which protrude distally and radially tube loops 18 and from them protrude wire loop distal ends 28, forming aperture 5.

Cutting element 70 is shown passing along sheath 12 and around tube loops distal ends 22, where it slidably passes through at least one permanent connector 72 and at least one detachable connector 71, said connectors typically attached to tube loops distal ends 22. Alternatively, said connectors may be attached to wire loop ends 28.

As evident from FIG. 6A, cutting element 70 expands radially with expansion of aperture 5, and is thus located at the leading edge of tube loops distal ends 22, surrounding any tissue dissected free from the artery by wire loops distal ends 28.

Figure 6C:
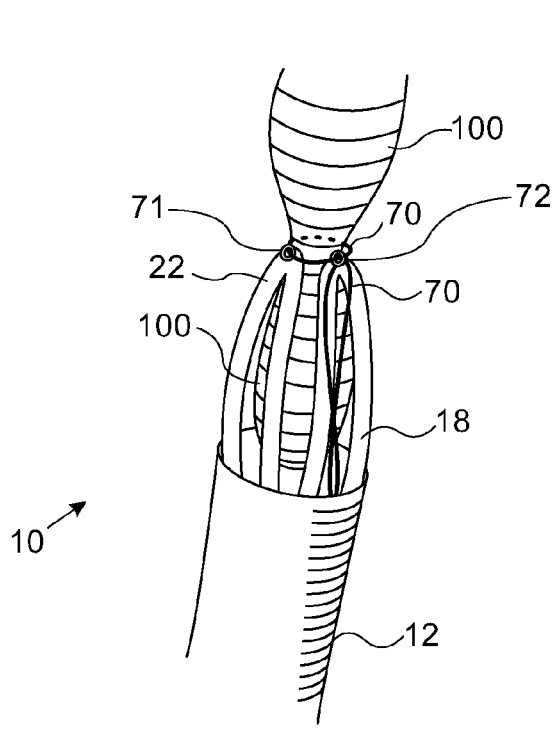
FIG. 6C shows the device of FIG. 6B in a constricted state containing the tissue, according to an embodiment of the invention.

FIG. 6C is a 3D depiction of the tip of device 10 in its closed state around the tissue at the distal end of a lesion.

More particularly, tube loops 18 are seen protruding distally out of sheath 12, and converging around tissue 100 which may be an intimal layer, an atherosclerotic plaque, or a different type of tissue if used for other applications.

Cutting element 70 is shown passing along sheath 12 and around tube loops distal ends 22, where it slidably passes through permanent connector 72 and detachable connectors 71. Not shown in this figure are wire loop distal ends 28 which also surround and constrict tissue 100.

The user now optionally activates cutting element 70, and pulls it proximally, causing it to be released from detachable connectors 71 and cut through tissue 100.

Figure 6D:
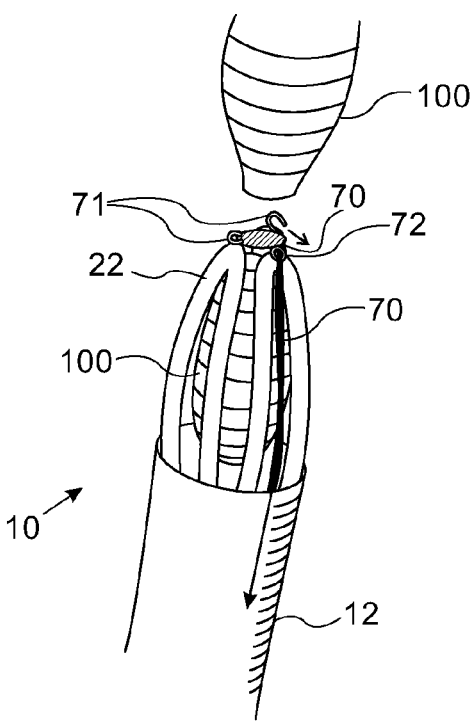
FIG. 6D shows the device of FIG. 6C after the cutting element has sheared the tissue, according to an embodiment of the invention.

FIG. 6D is a 3D depiction of the tip of device 10 in its closed state at the distal end of a lesion, after cutting element 70 has cut the tissue.

More particularly, tube loops 18 are seen protruding distally out of sheath 12, and converging around tissue 100.

Cutting element 70 is shown passing along sheath 12 and through permanent connector 72. It was released from detachable connectors 71, and cut through tissue 100. Not shown in this figure are wire loop distal ends 28 which also surround and constrict tissue 100.

In use, when device 10 is deployed, cutting element 70 slides through connectors 71 and 72 and opens as a loop around tube loops distal ends 22 (FIG. 6B). As it is thin, and does not protrude significantly to any side, cutting element 70 does not interfere with plaque separation.

Once separation of plaque is complete, wire loops 24 are pulled proximally by the user, causing tube loop ends 22 and wire loop ends 28 to tightly constrict around tissue 100 (FIG. 6C). Cutting element 70 is also pulled slightly proximally, such that it tightly encircles tissue 100.

As shown in FIG. 6D, cutting element 70 is then activated (by pulling it proximally if it is a wire, by "shifting" the leading segment to a sharp segment if it is a strip as described below, by transferring electrical current or a different energy form if it is an insulator, optic fiber or other means of energy transfer). Typically, cutting element 70 is then pulled proximally, slides through permanent connectors 72, and cuts detachable connectors 71 and tissue 100. FIG. 6D shows device 10 around a piece of tissue 100 after cutting element 70 was pulled proximally and cut the tissue around tube distal ends 22. Thus, the cutting element can include a blunt and a sharp state. In some embodiments, the cutting element can include a cutting and a non-cutting state. Further, the cutting element can be configured to transition between blunt and sharp states upon the aperture substantially closing.

Controlling the radial force at the aperture 5 adds versatility to use of device 10. Embodiments enabling control of the radial force, in either a predetermined, or an adjustable manner, are described in FIGS. 7A and 7B.

Figure 7A:
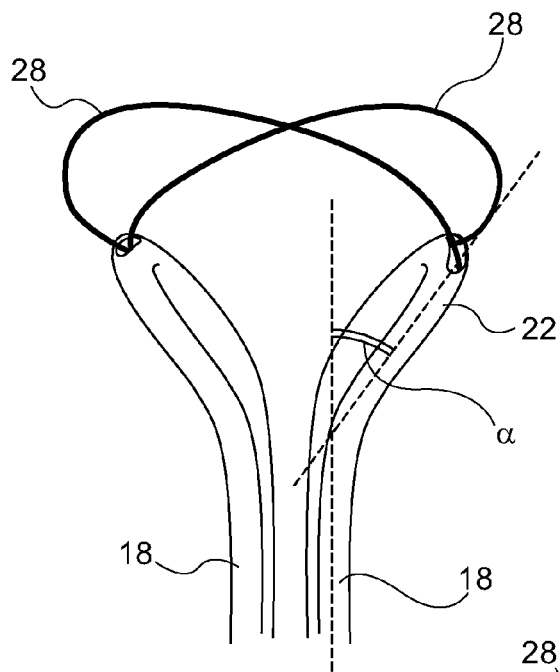
FIG. 7A shows a side view of a distal end of the loops of a device, according to an embodiment of the invention.

In an embodiment shown in FIG. 7A, tube loop distal ends 22 have an outwardly oriented curve at an angle α. This serves to increase the radial force applied to the arterial wall by the combined structure formed by tube loop distal ends 22 and wire loop distal ends 28. The greater the outward angle α, the greater the radial force.

More particularly, FIG. 7A is a schematic side view of the working end of device 10. For the sake of clarity only two sets of tube and wire loops are shown. Tube loops 18 are seen with wire loop distal ends 28 protruding therefrom. Angle α is the angle between the straight part of tube loop 18 and the outwardly curved part, tube loop distal end 22.

In an embodiment, wire loops 24 additionally, or only, have a similar curve to that described above.

In an embodiment, any of the above outward curves may be achieved by heat treatment of the tube and/or wire material.

In another embodiment, a segment of the tube is replaced or covered by a more rigid tube with the outwardly curved shape. In yet another embodiment, at least one wire is connected to tube loop distal ends 22, allowing control of the curvature, such that the curve can be increased by pulling this wire proximally.

Figure 7B:
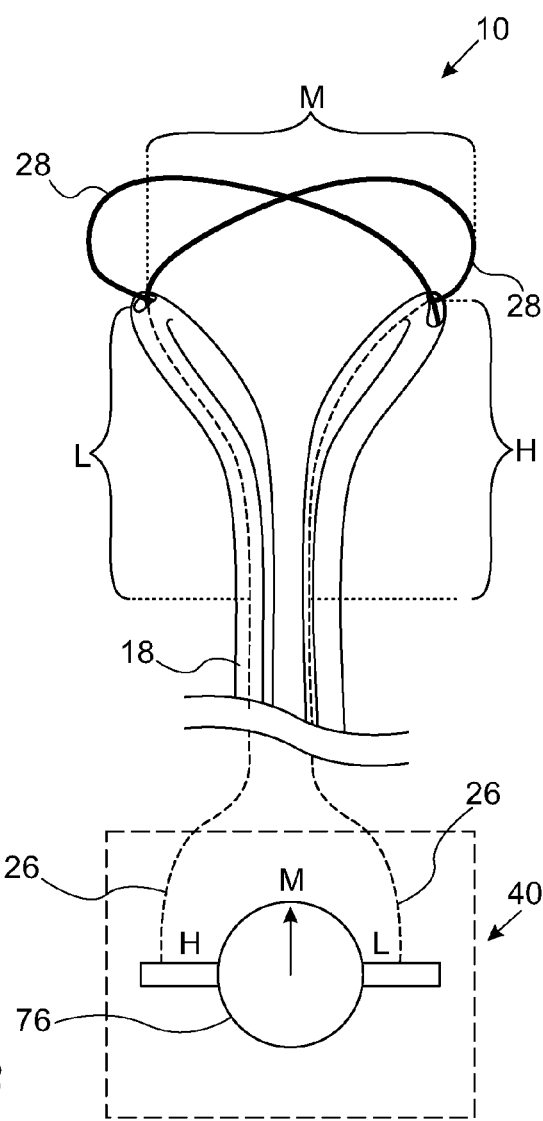
FIG. 7B shows a side view of a distal end of the loops of a device, according to an embodiment of the invention.

In an embodiment depicted in FIG. 7B, control of radial force is achieved by replacing, or "shifting" the segment of wire comprising wire loop distal end 28 (by pushing one side distally and pulling the other proximally), using wire loops 24 that have several segments with different levels of rigidity, shape or curvature, and optionally varying sharpness. The segment of wire loop 24 located at wire loop distal end 28 confers the desired rigidity to the distal end of device 10 and determines its radial force. Thus, the tool in the deployed state can have a radial force and the tool can be configured to allow adjustment of at least one of the radial force and the aperture. The at least one tube loop can have an adjustable outward angle and the adjustment of the radial force can take place by pushing the wire loop along a longitudinal axis of sheath. Further, the at least one wire loop can have varying degrees of rigidity/flexibility and the adjustment of the radial force can be by shifting a location of segments of the at least one wire loop.

Low rigidity and high flexibility are useful in the crimped state. Increasing degrees of rigidity can confer increasing radial force to the deployed device.

In an embodiment, one of the above segments may have a sharp inner edge, and may be brought to the leading end of the loop only when cutting of the end of the plaque is desired.

A control, which may for example consist of a rotating button on handle 40, may allow shifting of the wire segment comprising wire loop distal end 28, and thus determining the characteristics of aperture 5.

More particularly, FIG. 7B is a schematic side view of the working end of device 10 and handle 40. For the sake of clarity only two sets of tube and wire loops are shown. Tube loops 18 are seen with wire loop distal ends 28 protruding therefrom.

Wire loop proximal ends 26 are seen entering handle 40 and connecting to a rotating control button 76. In the current example button 76 has three positions each corresponding to the analogous segment on wire loop 24. Rotating button 76 to any of the positions, brings the corresponding wire segment to be at wire loop distal end. Optionally, one such button 76 controls all wire loops 24. Alternatively, each wire loop 24 is controlled separately.

Figure 8:
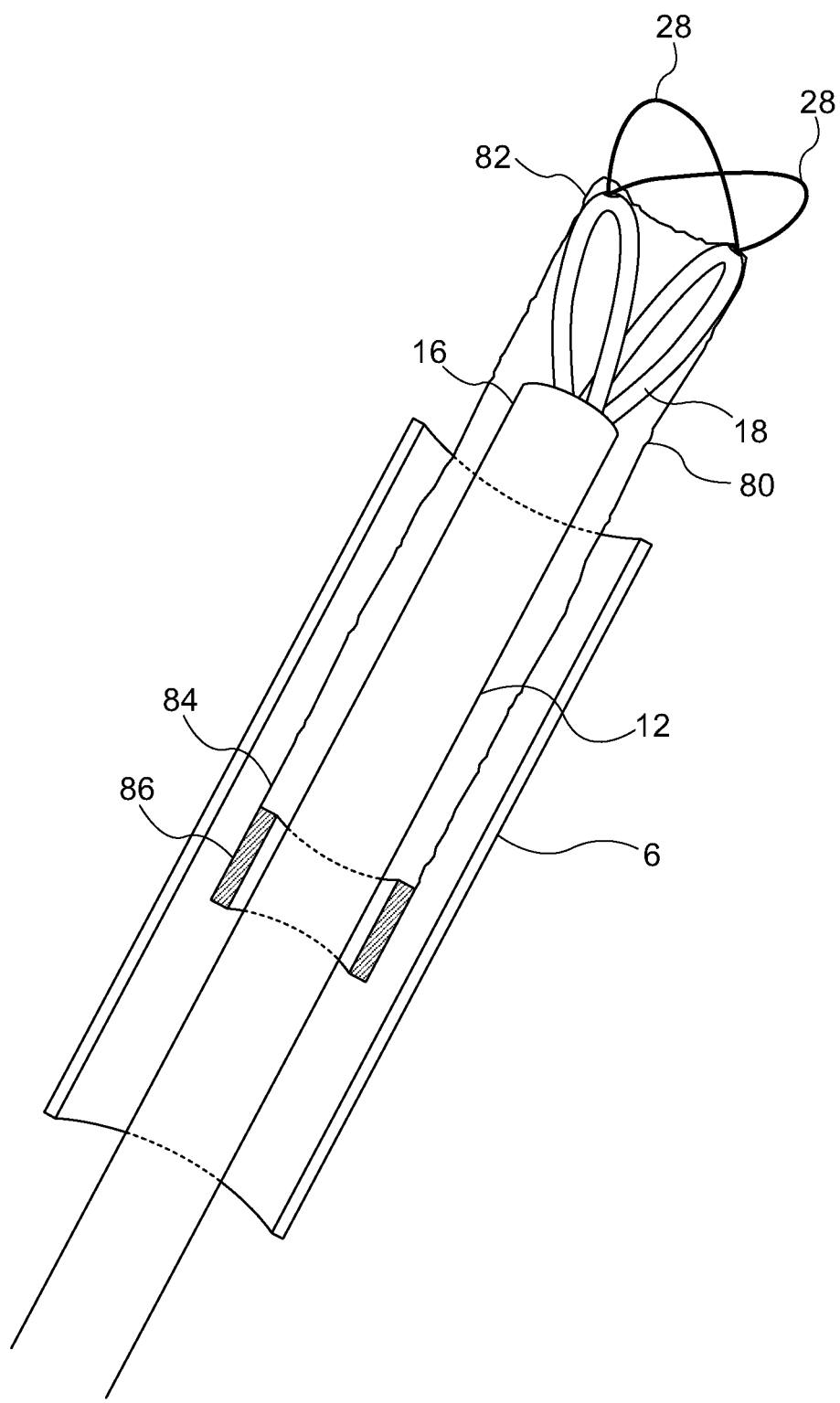
FIG. 8 shows a device in a deployed state having a sac, according to an embodiment of the invention.

In an embodiment shown in FIG. 8, a "compartment/sac" is used to contain the dissected plaque in order to remove it as a whole and prevent debris from falling off during removal. Such "compartment/sac" may for example consist of a thin sleeve made of polyurethane, silicone, latex, or any other thin membrane, a fine wire mesh, a fabric such as Gortex, etc.

More particularly, FIG. 8 is a schematic longitudinal section—side view of a guiding catheter 6, through which was passed the distal part of device 10 showing sheath 12 with tube loops 18 extending distally out of its distal end 16, and wire loop ends 28 protruding therefrom, creating aperture 5. Again for the sake of clarity, only two sets of loops and wires are shown. Sheath 12 may be slideably disposed within guiding catheter 6. A ring 86 may be slideably disposed between guiding catheter 6 and sheath 12. Sac 80, having distal end 82 and proximal end 84 may be slideably disposed over sheath 12, with its proximal end 84 connected to ring 86, and its distal end 82 connected at least at one point to tube loop distal ends 22. In another embodiment, sac 80 may be attached to tube loops 18 from ends 22 to proximal ends 20 and may have sufficient slack in it to allow for radial expansion of the loops and containment of large plaques or other excised tissue.

In yet another embodiment, sac 80 may be connected in at least one point to wire loop distal ends 28.

Sac 80 may further include a thickened or fortified rim at its distal end 82. This is typically a slightly thicker ring of the sac, made of the same material as the rest of the sac. For example, if the sac is made of 0.01 mm polyurethane, the rim may be created by folding sac 80 back and welding it to itself, so its thickness is ~0.02 mm. The rim may provide several advantages:

First, such fortified rim can serve as, or include, a connection element aiding in connection of sac 80 to wire loop distal ends 28.

Second, this fortified rim may cause sac 80 distal end 82 to assume a circular cross sectional shape when aperture 5 opens, instead of being stretched into assuming a polygonal cross section, which could interfere with its ability to follow the path of dissection taken by wire loop ends 28.

Returning to the embodiment shown in FIG. 8, sac 80 can advance along sheath 12 as tube loops 18 are pushed distally out of sheath 12. As it advances, the sac can surround and contain the tissue dissected away from the artery by wire loop ends 28 and tube loop ends 22. At the end of dissection, after the cutting stage, the distal end 82 of sac 80 closes with the closure of aperture 5, and the complete excised specimen may be removed as one, within sac 80.

Thus, as shown in FIG. 8, the device can include a sac 80 at least a portion of which is either disposed inside the sheath 12 or at least a portion of which is disposed outside a portion of the sheath 12. The sac is configured to enclose the at least one tube loop 18 and at least one wire loop 28 in the closed state. The sac 80 can be connected to at least one portion of the distal end 28 of the tube loop 18. The tool 41 can also include a ring 86 that is slideably disposed between the multilumen tube 30 and the sheath 12. The sac 80 can be connected to the ring 86. The sac can be connected to at least one portion of the distal end of the at least one tube loop.

Figure 9:
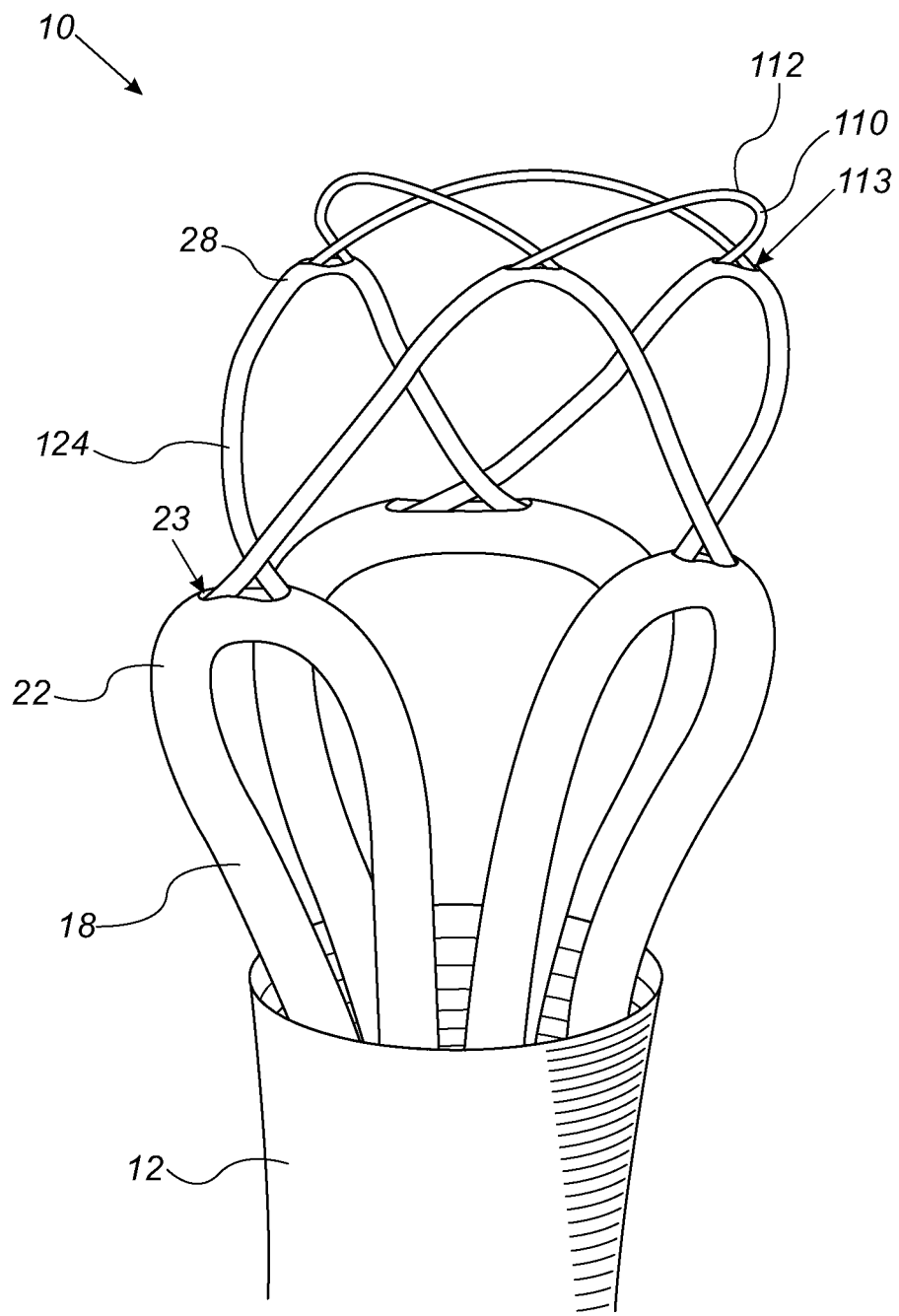
FIG. 9 shows a device in a deployed state having three layers of loops, according to an embodiment of the invention.

In an embodiment shown in FIG. 9, device 10 has a construction similar to that previously described in FIGS. 1-4, and in addition comprises an additional level of tube loops.

More particularly, FIG. 9 is a three dimensional depiction of the distal working end of device 10, showing only three sets of each level of loops, for the sake of clarity. From proximal to distal shown are the distal end of sheath 12, tube loops 18 protruding distally therefrom, having tube loops distal ends 22 and windows 23. Protruding from windows 23 are wire loops 24 ending with wire loop distal ends 28, however in this embodiment, these elements are made of hollow tubes or sheaths instead of wires, and have additional windows 113 at sheathwire loop distal ends 28. Slideably disposed within these tubes 124 are wire loops 110 having wire loop distal ends 112 protruding out of windows 113 in a manner similar to that described above for wire loop distal ends 28, windows 23, and tube loop distal ends 22.

The above configuration may be repeated many times with additional levels of tubes. This construction may provide greater versatility with a possibility of advancing each set of loops to different distances, and better control of device behavior in different areas, for example by widening the device to different diameters at different locations.

In general, the most distal level, consisting of wire loops may be used for dissection, whereas the more proximal levels consisting of tube loops may be pushed distally in an alternating fashion, which improves their ability to advance around the tissue.

Controlling this action manually may provide delicate haptic feedback to the physician, who can feel changes in resistance as the loops are advanced.

In an embodiment, an engine could be used to advance the various levels of loops by alternating motions, or by vibration.

Thus, the at least one tube loop and the at least one wire loop can include three levels of loops. For example, the tool can include a first level of at least one tube loop and a second level of at least one tube loop that proceeds from a distal end of the first level of the at least one tube loop in the deployed state. Further, the at least one wire loop can extend from the distal end of the second level of the at least one tube loop in the deployed state.

Figure 10:
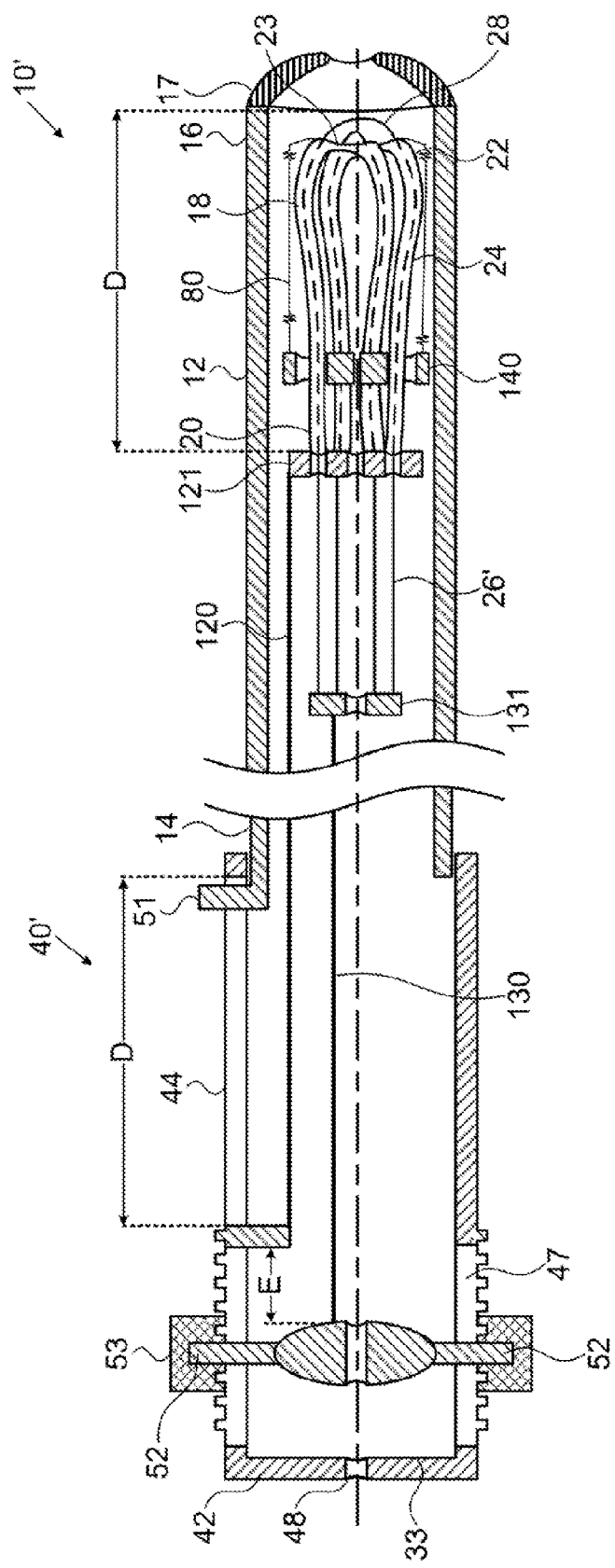
FIG. 10 shows a schematic longitudinal section of a device in a crimped state, according to an embodiment of the invention.

FIG. 10 shows device 10', which is generally similar to device 10 previously described in FIGS. 1A and 1B, with various modifications.

More particularly, FIG. 10 is a schematic longitudinal section of a preferred embodiment of device 10 in its crimped state, mainly comprising the following parts, from proximal to distal: handle 40', cables 120 and 130, tube connector 121 and wire connector 131, one or more tube loops 18 and one or more wire loops 24, which may be slideably disposed within a sheath 12 having proximal end 14 and distal end 16, short multilumen segment 140 also slideably disposed within sheath 12, sac 80, and optionally an atraumatic tip 17.

In this embodiment, tube cable 120 may have a distal end connected to tube connector 121 which may be slideably disposed within sheath 12, and a proximal end fixedly connected to elongate casing 42. Tube loops 18 may all be connected to tube connector 121 at their proximal end 20.

Sheath 12 may be slideably disposed within elongate casing 42, and can be withdrawn proximally by a tube handle 51, to expose tube loops 18.

Wire cable 130 may have a distal end connected to wire connector 131 which is slideably disposed within sheath 12, and a proximal end connected to wire handle 52. Wire loops 24 may all be connected to wire connector 131 at their proximal end 26'. Thus, pushing wire handle 52 distally, may deploy wire loop distal ends 28 and open aperture 5.

Wire handle 52 may protrude outwardly of casing 42 through slot 47. Since in the current embodiment, handle 52 does not move together with tube handle 50 as in the embodiment shown in FIG. 1, slot 47 does not need to be long as did slot 46.

Short multilumen segment 140 (a few millimeters long) may optionally be placed proximal to the distal end 16 of sheath 12, such that tube loops 18 pass through its peripheral lumens 145, maintaining an organized configuration of the tubes.

Sac 80 can be stored within sheath 12, folded in the gap between distal end 16 and the short multilumen segment 140. Short multilumen segment 140 can be pushed distally out of sheath 12 up almost its whole length. Alternatively, short multilumen segment 140 may be fixedly connected to the interior of sheath 12. Thus, the device can further include a multilumen segment that is configured to house a portion of the at least one tube loop. The device can further include connections between each of adjacent tube loops. The connections can be distal to the multilumen segment.

An advantage of this design is that wire handle 52 does not move relative to casing 42 during advancement of tube loops 18.

Another advantage of this design is that tube cable 120 and wire cable 121 can be relatively thick and rigid yet flexible wires, which are more resistant to buckling than long segments of thin wire and tubes as in FIG. 1A, and are cheaper than multiple thin wires, tubes, or multilumen catheter.

It should be noted that in this embodiment, advancement of deployed wire loops 24 and tube loops 18 around the plaque may be performed by moving the whole device handle 40 distally, which increases the treating physician's ability to collect tactile information from the device and control the procedure.

Adding control and accuracy to the opening and closing of aperture 5 can be done by adding a threaded button 53 to handle 40. As shown in FIG. 10, threaded button 53 may be slideably positioned over elongate casing 42, having an inner thread, and may have a slot for receiving handles 52. Elongate casing 42 may have an external thread along slot 47. This construction allows exact control of the deployment of wire loops 24 by rotating threaded button 53, which may move wire connector 33 axially without rotating it.

Another advantage of using this type of control is that it allows application of tensile forces to wire loops 24, which are typically made of nitinol and therefore are capable of great elongation. This may necessitate pulling wire connector 33 proximally beyond its original position, for complete closure of aperture 5, especially if closing it over tissue with a large diameter or having tough consistency. To facilitate this, the initial position of wire handle 52 in the crimped state of device 10 before use may not be at the proximal end of slot 47 and its external thread, rather, there may be sufficient range of movement to either side along slot 47, so as to allow for the compensation for wire loop 24 elongation.

When high axial stresses are encountered by the leading edge of the device (wire loop distal ends 28), there may sometimes be a tendency of the more proximal tube loops 18 to buckle and collapse. This buckling can occur within sheath 12, or distal to it.

Several ways of preventing this are described:

Prevention of tube loop buckling within sheath 12 can be achieved for example by gradual reinforcement of tube loops 18 towards their proximal end. Such reinforcement can be done by increasing tube wall thickness, adding a layer of braid, adding a coating, using more rigid wires in the HHS braid, etc.

Another way of preventing buckling within sheath 12 comprises reducing the available space around the tubes. This can be done either by minimizing the inner diameter of the sheath, or by adding a central core, or tube, that will support tube loops 18, such that they are compressed between it and the sheath.

Using an inflatable balloon instead of said core or tube, may enable temporarily splinting tube loops 18 to the inner side of sheath 12. Such splinting may also be beneficial for increasing the torquability of the device. For example, if the user wishes to rotate the working end of the device, inflating said balloon may increase transfer of torque to wire loop distal ends 28, so that they may rotate with rotation of handle 40.

A similar method of supporting tube loops 18 can be used outside sheath 12, once the tubes have exited it and are within the vessel lumen. Inflating an elongate balloon in the vessel just distal to sheath distal end 16 may provide support to the tubes and reduce their tendency to buckle.

Another problem that may occur with construction of the device of the invention relates to correct opening of aperture 5.

If wire loops 24 and/or tube loops 18 are coiled at a relatively small radius along their longitudinal axis, they may tend to swivel to the same orientation around the long axis of the device. If this occurs, when opening aperture 5, the structure formed may not be an open aperture, rather it may be collapsed, having a cross section shaped as a concave polygon.

Preventing this can be done by ensuring that the elongate elements (wires, tubes, sheath) of the device are straight, or at least have a large diameter of curvature—e.g. approximately 100 cm diameter of curvature for a device with a 10 french (3.3 mm) outer diameter. This may require keeping the device in an elongate or large diameter packaging.

A modification mentioned previously—adding the short multilumen segment 140 proximal to sheath distal end 16, can maintain correct orientation and order of tube loops 18 and thus assist in preventing this issue.

Another possible solution is including a directional feature on tube loops 18 that forces them to maintain the correct orientation.

Figure 11:
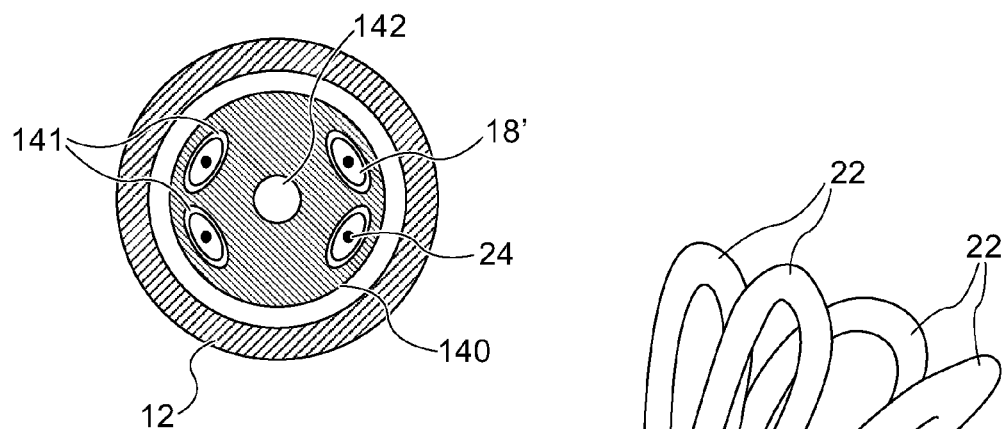
FIG. 11 shows schematic cross sectional view of device at the middle of a multilumen segment having a directional feature, according to an embodiment of the invention.

FIG. 11 describes an example of this embodiment.

More particularly, FIG. 11 is a simplified schematic cross sectional view of device 10' at the middle of short multilumen segment 140, showing only two sets of tubes, for the sake of clarity. From the periphery to the center of the figure are seen sheath 12, short multilumen segment 140 slideably disposed therein, said segment 140 having peripheral lumens 141 and central lumen 142. Peripheral lumens 141 may have an oval cross sectional shape. Slideably disposed within peripheral lumens 141 are tube loops 18', which may have an oval cross sectional shape too, corresponding to that of peripheral lumens 141. Slideably disposed within tube loops 18' are wire loops 24.

The oval cross sectional shapes of tube loops 18' and peripheral lumens 141 serve as directional features which may ensure that the order and orientation of tube loop distal ends 22 are maintained at they pass distal end 16 of sheath 12, thereby ensuring correct opening of aperture 5.

To create the oval cross sectional shape, tubes 18 may be processed, for example by being compressed along at least a part of their length so as to change their cross section from circular to oval.

Other directional features that can be used instead of the oval cross section include but are not limited to square, oblong, triangular, crescent, and u shaped cross sections, as well as longitudinal directional features. Thus, the tool can include a directional feature that ensures order and orientation of the at least one tube loop. A directional feature can include the tube loop having a portion with an oval cross-sectional shape and a central lumen of the multilumen segment having an oval cross-sectional shape.

Figure 12A:
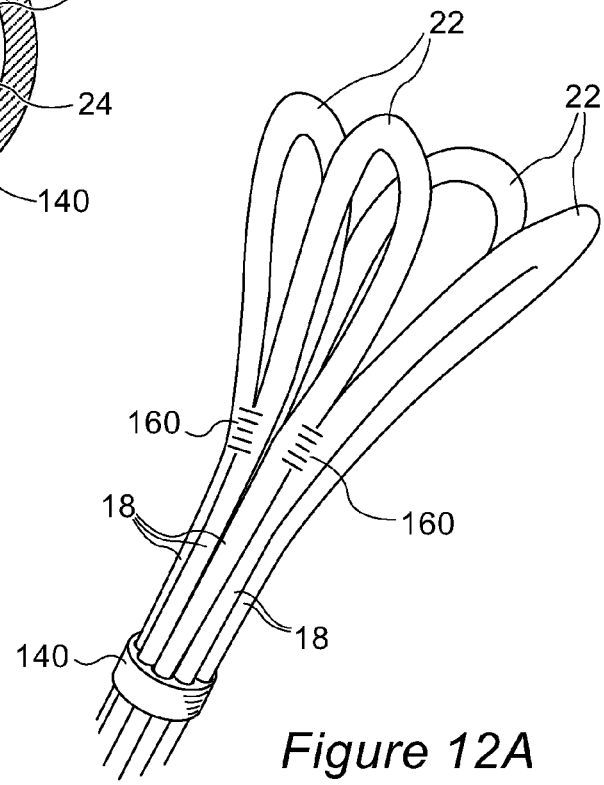
FIG. 12A is a schematic 3D depiction of the distal end of tube loops 18 in an almost crimped state of the device, according to an embodiment of the invention.
Figure 12B:
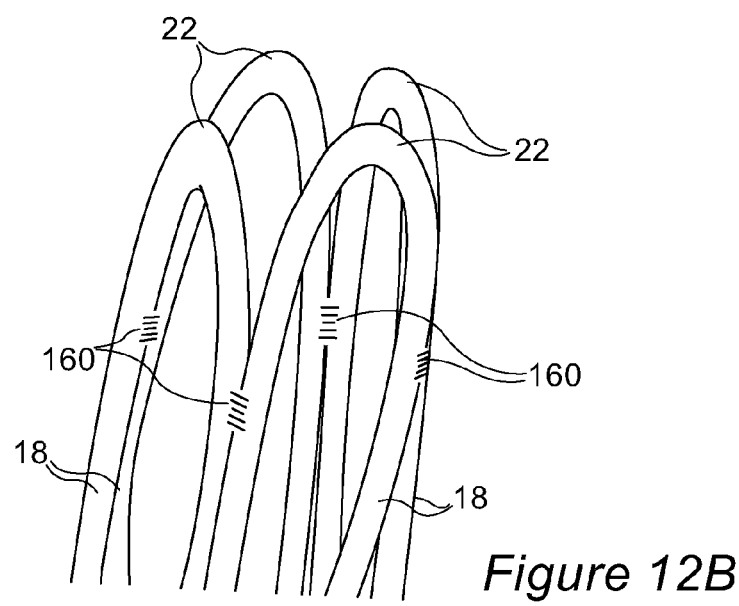
FIG. 12B is a schematic 3D depiction of the distal end of tube loops 18 in an almost deployed state of the device, according to an embodiment of the invention.

Another way to prevent the problem of the aperture opening flatly is depicted in FIGS. 12A and 12B—that is, by adding connections between each two adjacent tube loop ends, just distal to short multilumen segment 140. The combination of this connection between the tube loops, with passing the loops proximally through the multilumen, ensures the orientation of the loops will be kept, and chances of buckling can be significantly reduced.

FIG. 12A is a schematic 3D depiction of the distal of tube loops 18 in an almost crimped state of the device.

More particularly, short multilumen segment 140 is seen, through which may pass multiple tube loops 18, ending as tube loop distal ends 22. Connections 160 are seen joining each two adjacent tube loops 18, distal to short multilumen segment 140.

Sheath 12 is not shown, for clarity. Typically, short multilumen segment 140 is positioned within sheath 12, a few centimeters proximal to its distal end 16. Also not show are windows 23, and wire loop distal ends 28.

FIG. 12B is a schematic 3D depiction of the distal of tube loops 18 in an almost deployed state of the device.

More particularly, multiple tube loops 18 are seen, ending as tube loop distal ends 22. Connections 160 are seen joining each two adjacent tube loops 18.

Short multilumen segment 140, sheath 12, windows 23, and wire loop distal ends 28 are not shown, for clarity.

Connections 160 may typically be made by laser welding tube loops 18, adhesion, or any other method as known in the art.

Connections 160 reinforce the structure created by tube loops 18, and when combined with short multilumen segment 140, this structure becomes even stronger.

Connections 160 do not interfere with passage of loops 18 through short multilumen segment 140, as they are distal to it.

Another possible way of solving this issue may be creating a weak adhesion between tube loops 18, such that they form one elongate structure. Such a structure may be more resistant to buckling, but may be easily separated from its distal end, when aperture 5 is opened by pushing wire loops 24 distally. A drawback of this method is that it may only work for a single deployment.

The above embodiments assume that during use of device 10, in its deployed state, the radial force applied by wire loop distal ends 28 against the arterial wall combined with distal pushing and rotation applied by the user, the wire loops will dissect between the plaque and arterial wall into the subintimal space. In some embodiments, the radial force of the wire loops and tube loops, together with pushing forward and some rotation, can result in the wire loops going into the path of least resistance, in the case of an atherosclerotic plaque, into the subintimal space.

The following embodiments are intended to facilitate this process.

Figure 13:
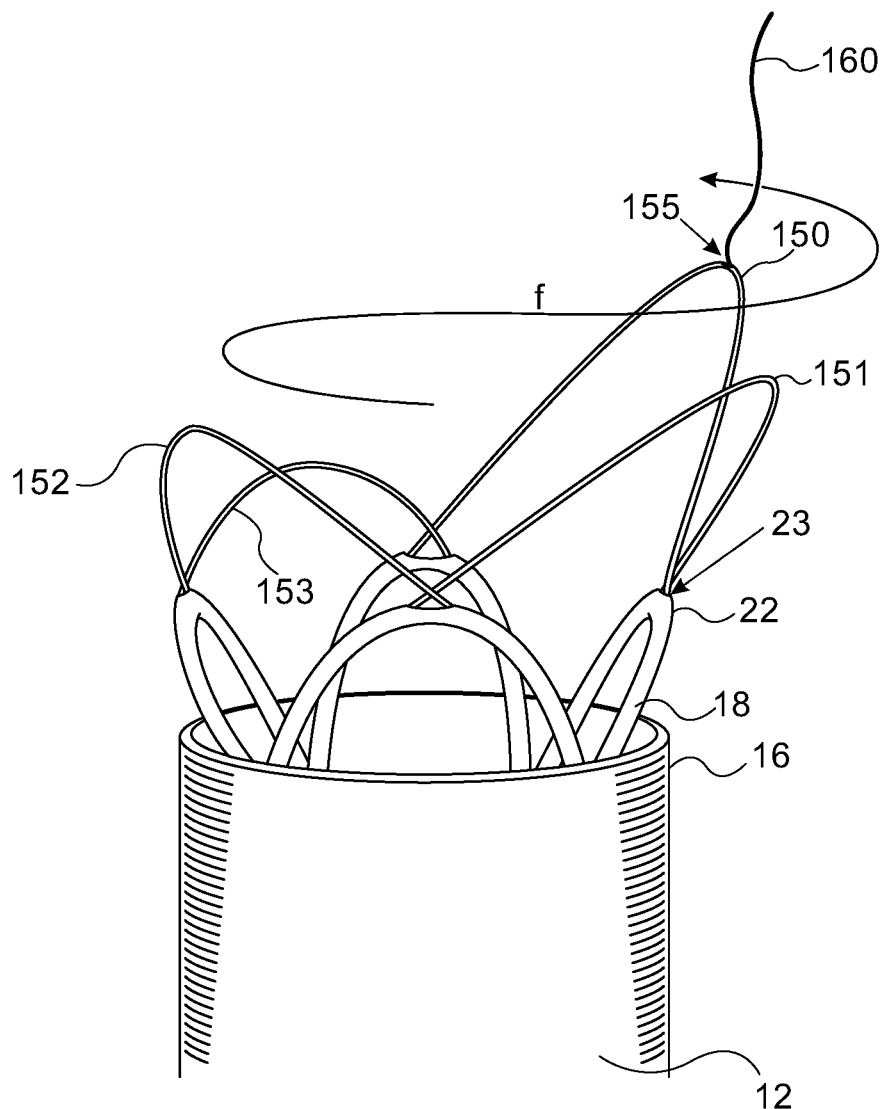
FIG. 13 shows a distal end of the medical device in a deployed state having graded loops, according to an embodiment of the invention.

FIG. 13 depicts an embodiment having a graded wire loop distal ends structure to improve entry of device 10 into the SIS. Thus, the at least one wire loop can be graded in the deployed state. The graded wire loops can protrude from the distal end of the sheath at varying distances. The at least one wire loop can have a graded distance between a most distal wire loop distal end and a most proximal wire loop distal end. The graded distance can provide improved entry of the tool to the subintimal space.

More particularly, FIG. 13 is a 3D depiction of distal end of device 10, showing sheath 12, with four tube loops 18 protruding from sheath distal end 16. Wire loop distal ends 150 to 153 exit tube loop distal ends 22 through windows 23, each protruding gradually less distally than the wire loop distal end next to it, such that wire loop distal end 150 may be the most distal, and wire loop distal end 153 may be the most proximal, thus creating a spiral formation.

In use, wire loop distal end 150 may be the first to enter the subintimal space, and each adjacent loop may follow as the device is advanced and rotated in the direction of arrow f.

To further improve entry into the SIS, a guidewire window 155 is provided at wire loop distal end 150, which in this case may be made of a hollow tube or sheath.

In use, optionally, a guidewire may first be inserted into the SIS under angiography as known in the art, and subsequently device 10 may be inserted over the guidewire by passing the guidewire into window 155 and all the way through device 10. This may ensure that wire loop distal end 150 easily enters the SIS.

Although described in the context of percutaneous remote endarterectomy, the devices of the invention may also be used and are intended for use for various other medical applications, including but not limited to the following:

Blood Clot Removal:

In situations where a blood clot clogs an artery or vein, there is a need for a minimally invasive technique for removal of such clot. This need is especially important in acute massive pulmonary embolism, which is a severe, life threatening condition due to hemodynamic compromise. Thus, the device can be configured for the minimally invasive removal of tissue in a pulmonary embolism.

Whereas various atherectomy devices have been used in an attempt to treat pulmonary embolism, these devices are not ideally suited for clot removal.

As described in the article: "Catheter-assisted pulmonary embolectomy.", Sobieszczyk P, Circulation. 2012 Oct. 9; 126(15):1917-22.

"The disadvantage of endovascular therapies lies in the size mismatch between the caliber of the proximal pulmonary arteries and the size of endovascular devices designed for thrombus removal from much smaller coronary or peripheral vessels or dialysis fistulas. In addition, to be accessible to catheter assisted embolectomy, the pulmonary embolism has to be located in the main pulmonary arteries or in the proximal segmental branches."

Thus, the device of embodiments of the invention can be configured for the minimally invasive removal of tissue in an embolectomy or thrombectomy.

The device of the invention is capable of removing and containing fresh clot trapped in the pulmonary arteries or their branches. In addition, it may also be used for removing older clot, which typically becomes similar to atherosclerotic lesions. Use of the device of the invention in these cases is similar to its use for endarterectomy, as described above.

Urinary Stone Removal:

Devices for removing urinary calculi are often designed as baskets. One of the drawbacks of some of these devices is that the stones might fall between the struts of the baskets. The device of the invention solves this issue by encasing the stone from all sides by the tube loops 18 as well as by the sac 80. Thus, the device can be configured for the minimally invasive removal of tissue in a urolithotomy procedure.

Other Applications:

The device of the invention may additionally be used for removal of bezoars from the GI tract, removal of foreign bodies from the bronchial tree or from any other body lumen.

Thus, methods of use and embodiments of the present invention can be directed to a method for minimally invasively removing tissue from a body lumen, which includes: passing a tool through a sheath that is configured to transition from a crimped state to a deployed state and to a closed state, a distal end of the tool having at least one tube loop and at least one wire loop; forming an aperture at a distal end of the tool in the deployed state; and dissecting tissue in the deployed state.

The method can be such that the forming the aperture includes extending the wire loops. The extending the at least one wire loop can include advancing the at least one wire loops through at least one window of the at least one tube loop. The passing the tool through the sheath can include transitioning to an expanded state. In some embodiments, passing the tool does not transition the tool into the expanded state until the wire loops are pushed.

The tissue can be a lesion and the method can further include extending the tool along the lesion. The dissecting can include dissecting the lesion along a longitudinal axis of the body lumen.

The method can further include closing the aperture distal to the dissected tissue to contain the tissue; and removing the tissue in the closed state.

The tool can include a handle at a proximal portion of the sheath; and a multilumen tube disposed inside at least a portion of the sheath, the multilumen tube being configured to interface with the at least one tube loop, and the method can further include passing the tool through the distal end of the sheath using movement of the handle.

The handle can include an elongate casing having a wire handle connected to the at least one wire loop and a slot for the wire handle to slide. The multilumen tube can be disposed inside at least a portion of the casing. The method can further include enclosing the loops with a sac in the closed state.

The method can further include passing the at least one wire loop through windows of the at least one tube loop in the deployed state.

The method can further include utilizing a cutting element to remove the tissue. The method can further include inserting a wire loop into the subintimal space of the tissue; and threading a leading wire loop distal end over a wire which has been inserted into the subintimal space of the tissue.

The method can further include: housing at least a portion of the at least one tube loop with a multilumen segment; and providing connections between each of adjacent tube loops distal to the multilumen segment.

The at least one tube loop can have a graded distance of the distal ends for the tool's improved entry to the subintimal space of the tissue.

The minimally invasive removal of tissue can include an endarterectomy. The minimally invasive removal of tissue can include an embolectomy. The minimally invasive removal of tissue can treat a pulmonary embolism. The minimally invasive removal of tissue can include a percutaneous procedure. The minimally invasive removal of tissue can include a urolithotomy.

The cutting element can be further defined as follows:

A cutting element, comprising:
a wire that is configured to extend around a distal portion of a tool configured to pass through a sheath and configured to transition from a crimped state to a deployed state and to a closed state, the distal portion of the tool forming an aperture;
a plurality of connectors that is configured to receive the wire,
wherein at least one of the plurality of connectors is a permanent connector and at least one of the plurality of connectors is a detachable connector, and
wherein when tension is exerted to the wire, the at least one permanent connector is configured to pass the wire to radially constrict the wire, and the at least one detachable connector is configured to release the wire, wherein the wire is operable to cut tissue inside the aperture.

While various exemplary embodiments have been described above, it should be understood that they have been presented by way of example only, and not limitation. Thus, the breadth and scope of the present disclosure should not be limited by any of the above-described exemplary embodiments, but should instead be defined only in accordance with the following claims and their equivalents.

What is claimed is:

1. A medical device for minimally invasive removal of tissue from a body lumen, comprising:
a sheath having a proximal and a distal end; and
a tool configured to pass through the sheath and configured to transition from a crimped state to a deployed state and to a closed state, wherein the tool forms an aperture at a distal end, the distal end of the tool having at least one tube loop and at least one wire loop, wherein the at least one wire loop extends distally from the at least one tube loop to form the aperture in the deployed state, and
wherein the tool is configured to dissect tissue in the deployed state.

2. The device of claim 1, wherein the tissue is a lesion and the tool is configured to extend along the lesion and is configured to dissect around the lesion along a longitudinal axis of the body lumen.

3. The device of claim 2, wherein the tool is configured to close the aperture distal to the dissected tissue to contain the tissue, wherein the tool is configured to remove the tissue in the closed state.

4. The device of claim 1, wherein the tool comprises a plurality of tube loops and a plurality of wire loops.

5. The device of claim 4, wherein the wire loops are moveable to a plurality of locations with respect to a radial axis of the sheath, wherein the wire loops are configured to contact each other, and wherein the wire loops are configured to close such that a scissor action between adjacent wires is operable to cut intima of the tissue.

6. The device of claim 4, wherein in a radial axis of the sheath each wire loop extends under another wire loop and over another wire loop.

7. The device of claim 6, wherein each tube loop has a first and a second wire loop, and wherein from a distal end view in the radial axis of the sheath, the second wire loop extends under the first wire loop in a clockwise direction of the radial axis of the sheath.

8. The device of claim 6, wherein each of a first set of two opposing wire loops extends over one of a second set of opposing wire loops, and each of the second set of opposing wire loops extends under one of the first set of opposing wire loops in a radial axis of the sheath.

9. The device of claim 6, wherein one wire loop extends over adjacent wire loops and an opposing wire loop extends under adjacent wire loops.

10. The device of claim 6, wherein each wire loop has a pre-formed curvature around a radial axis of the sheath, the curvature being radially displaced from a longitudinal axis of the sheath.

11. The device of claim 10, wherein at least one of the wire loops extends over at least another wire loop and at least one of the wire loops extends under at least another of the wire loops in the radial axis of the sheath.

12. The device of claim 11, wherein a first wire loop extends over all other wire loops and other wire loops are interlaced with adjacent wire loops in the radial axis of the sheath, wherein the first wire loop when retracted is configured to pass a center line of the body lumen.

13. The device of claim 11, wherein each tube loop has a first wire loop that extends in a counter-clockwise direction of the radial axis of the sheath and a second wire loop that extends in a clockwise direction of the radial axis of the sheath.

14. The device of claim 13, wherein the first and second wire loops cross each other in the radial axis.

15. The device of claim 13, wherein the first and second wire loops do not cross each other in the radial axis.

16. The device of claim 6, wherein the at least one wire loop is graded in the deployed state, the graded wire loops protruding from the distal end of the sheath at varying distances.

17. The device of claim 16, wherein the wire loops have a graded distance between a most distal wire loop distal end and a most proximal wire loop distal end, the graded distance providing improved entry of the tool to subintimal space.

18. The device of claim 1, wherein the at least one tube loop has a window that allows for passage of the at least one wire loop.

19. The device of claim 18, wherein the window of the at least one tube loop is a distal window and outlines two holes.

20. The device of claim 19, wherein the at least one tube loop has a longitudinal axis, and the distal window has a length along the longitudinal axis in a range between about 0.5 to about 5 times a diameter of the at least one tube loop.

21. The device of claim 1, wherein the at least one tube loop comprises four spatially equidistant loops.

22. The device of claim 1, wherein the at least one tube loop comprises anywhere from two through eight loops.

23. The device of claim 1, further comprising:
a handle at a proximal portion of the sheath; and
a multilumen tube disposed inside at least a portion of the sheath, the multilumen tube being configured to interface with the at least one tube loop,
wherein the tool is configured to pass through the distal end of the sheath using movement of the handle.

24. The device of claim 23, wherein the handle comprises an elongate casing having a wire handle connected to the at least one tube loop and a slot for the wire handle to slide, and wherein the multilumen tube is disposed inside at least a portion of the casing.

25. The device of claim 23, further comprising a sac that is configured to enclose the at least one tube loop and at least one wire loop in the closed state.

26. The device of claim 25, wherein at least a portion of the sac is disposed inside the sheath.

27. The device of claim 25, wherein at least a portion of the sac is disposed outside the sheath.

28. The device of claim 27, further comprising a ring that is slideably disposed between the multilumen tube and the sheath, wherein the sac is connected to the ring.

29. The device of claim 25, wherein the sac is connected to at least one portion of the distal end of the at least one tube loop.

30. A method for minimally invasively removing tissue from a body lumen using the device of claim 1, comprising:
   passing the tool through the sheath that is configured to transition from the crimped state to the deployed state and to the closed state;
   forming the aperture at the distal end of the tool in the deployed state; and
   dissecting the tissue in the deployed state.

\* \* \* \* \*

UNITED STATES PATENT AND TRADEMARK OFFICE
CERTIFICATE OF CORRECTION

PATENT NO.       : 9,693,795 B2
APPLICATION NO.  : 15/167629
DATED            : July 4, 2017
INVENTOR(S)      : Itzhak Avneri et al.

It is certified that error appears in the above-identified patent and that said Letters Patent is hereby corrected as shown below:

In the Drawings

In Sheet 20, Fig. 13, the reference numeral 160 should be changed to reference number 170, as shown on attached sheet.

In the Specification

In Column 12, Line 52, "tube loops 14" should be --tube loops 18--.

In Column 23, Line 22, "wire loops 24" should be --wire loops 124--.

In Column 24, Line 39, "wire cable 121" should be --wire cable 130--.

In Column 27, Line 33, "guide wire" should be --guide wire 170--.

Signed and Sealed this
Tenth Day of October, 2017

Joseph Matal
*Performing the Functions and Duties of the*
*Under Secretary of Commerce for Intellectual Property and*
*Director of the United States Patent and Trademark Office*